(12) United States Patent
Xie et al.

(10) Patent No.: US 10,596,523 B2
(45) Date of Patent: Mar. 24, 2020

(54) METHODS AND APPARATUS FOR FORMING APERTURES IN A SOLID STATE MEMBRANE USING DIELECTRIC BREAKDOWN

(71) Applicant: Oxford Nanopore Inc., Cambridge, MA (US)

(72) Inventors: Ping Xie, Cambridge, MA (US); Ken Healy, Cambridge, MA (US); Justin Millis, Cambridge, MA (US)

(73) Assignee: Oxford Nanopore Inc.

( * ) Notice: Subject to any disclaimer, the term of this patent is extended or adjusted under 35 U.S.C. 154(b) by 102 days.

(21) Appl. No.: 15/575,798

(22) PCT Filed: May 20, 2016

(86) PCT No.: PCT/US2016/033487
§ 371 (c)(1),
(2) Date: Nov. 20, 2017

(87) PCT Pub. No.: WO2016/187519
PCT Pub. Date: Nov. 24, 2016

(65) Prior Publication Data
US 2018/0141007 A1    May 24, 2018

(30) Foreign Application Priority Data
May 20, 2015 (GB) .................................. 1508669.7

(51) Int. Cl.
*B01D 67/00* (2006.01)
*B01D 69/02* (2006.01)
(Continued)

(52) U.S. Cl.
CPC ......... *B01D 67/0062* (2013.01); *B01D 69/02* (2013.01); *B01D 69/06* (2013.01);
(Continued)

(58) Field of Classification Search
None
See application file for complete search history.

(56) References Cited

U.S. PATENT DOCUMENTS

| | | |
|---|---|---|
| 6,627,067 B1 | 9/2003 | Branton et al. |
| 8,698,481 B2 | 4/2014 | Lieber et al. |

(Continued)

FOREIGN PATENT DOCUMENTS

| | | |
|---|---|---|
| KR | 20120000520 A | 1/2012 |
| WO | WO 2000/028312 A1 | 5/2000 |

(Continued)

OTHER PUBLICATIONS

Beamish et al., Precise control of the size and noise of solid-state nanopores using high electric fields. Nanotechnology. Oct. 12, 2012;23(40):405301. Epub Sep. 14, 2012.

(Continued)

*Primary Examiner* — Krishnan S Menon
(74) *Attorney, Agent, or Firm* — Wolf, Greenfield & Sacks, P.C.

(57) ABSTRACT

Methods and apparatus for forming apertures in a solid state membrane using dielectric breakdown are provided. In one disclosed arrangement a plurality of apertures are formed. The membrane comprises a first surface area portion on one side of the membrane and a second surface area portion on the other side of the membrane. Each of a plurality of target regions comprises a recess or a fluidic passage opening out into the first or second surface area portion. The method comprises contacting all of the first surface area portion of the membrane with a first bath comprising ionic solution and all of the second surface area portion with a second bath comprising ionic solution. A voltage is applied across the membrane via first and second electrodes in respective contact with the first and second baths comprising ionic (Continued)

solutions to form an aperture at each of a plurality of the target regions in the membrane.

21 Claims, 8 Drawing Sheets

(51) Int. Cl.
```
      C25F 7/00        (2006.01)
      G01N 33/487      (2006.01)
      B01D 69/06       (2006.01)
      C25F 3/02        (2006.01)
      B01D 69/12       (2006.01)
      C12Q 1/6869      (2018.01)
      C25F 3/14        (2006.01)
      B82Y 40/00       (2011.01)
```
(52) U.S. Cl.
CPC ........... *B01D 69/12* (2013.01); *C12Q 1/6869* (2013.01); *C25F 3/02* (2013.01); *C25F 3/14* (2013.01); *C25F 7/00* (2013.01); *G01N 33/48721* (2013.01); *B01D 2323/42* (2013.01); *B01D 2325/021* (2013.01); *B01D 2325/06* (2013.01); *B82Y 40/00* (2013.01)

(56) References Cited

U.S. PATENT DOCUMENTS

| | | | |
|---|---|---|---|
| 8,828,138 | B2 | 9/2014 | Bedell et al. |
| 8,828,211 | B2 | 9/2014 | Garaj et al. |
| 2011/0053284 | A1 | 3/2011 | Meller et al. |
| 2013/0309776 | A1 | 11/2013 | Drndic et al. |
| 2014/0174927 | A1 | 6/2014 | Bashir et al. |
| 2014/0262820 | A1* | 9/2014 | Kuan ............... C25F 3/14 205/665 |
| 2015/0108008 | A1* | 4/2015 | Kwok ............... B01D 65/02 205/644 |
| 2017/0138899 | A1 | 5/2017 | Itabashi et al. |
| 2017/0315109 | A1* | 11/2017 | Alden .............. G01N 33/54366 |

FOREIGN PATENT DOCUMENTS

| | | |
|---|---|---|
| WO | WO 2003/003446 A2 | 1/2003 |
| WO | WO 2005/124888 A1 | 12/2005 |
| WO | WO 2007/041621 A2 | 4/2007 |
| WO | WO 2008/102120 A1 | 8/2008 |
| WO | WO 2008/124107 A1 | 10/2008 |
| WO | WO 2009/020682 A2 | 2/2009 |
| WO | WO 2009/035647 A1 | 3/2009 |
| WO | WO 2009/077734 A2 | 6/2009 |
| WO | WO 2010/122293 A1 | 10/2010 |
| WO | WO 2011/040996 A1 | 4/2011 |
| WO | WO 2011/067559 A1 | 6/2011 |
| WO | WO 2012/125770 A2 | 9/2012 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/121224 A1 | 8/2013 |
| WO | WO 2013/123379 A2 | 8/2013 |
| WO | WO 2013/153359 A1 | 10/2013 |
| WO | WO 2013/167952 A1 | 11/2013 |
| WO | WO 2013/167955 A1 | 11/2013 |
| WO | WO 2014/064443 A1 | 5/2014 |
| WO | WO 2014/144818 A2 | 9/2014 |
| WO | WO 2015/152003 A2 | 10/2015 |
| WO | WO 2016/034591 A2 | 3/2016 |

OTHER PUBLICATIONS

Briggs et al., Automated fabrication of 2-nm solid-state nanopores for nucleic acid analysis. Small. May 28, 2014;10(10):2077-86. doi:10.1002/smll.201303602. Epub Mar. 2, 2014.

Briggs et al., Kinetics of nanopore fabrication during controlled breakdown of dielectric membranes in solution. Nanotechnology. Feb. 27, 2015;26(8):084004. doi: 10.1088/0957-4484/26/8/084004. Epub Feb. 4, 2015.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

George, Atomic layer deposition: an overview. Chem Rev. Jan. 2010;110(1):111-31. doi: 10.1021/cr900056b.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Ivanov et al., DNA tunneling detector embedded in a nanopore. Nano Lett. Jan. 12, 2011;11(1):279-85. doi: 10.1021/nl103873a. Epub Dec. 6, 2010.

Kwok et al., Long Passage Times of Short ssDNA Moiecuies through Metallized Nanopores Fabricated by Controlled Breakdown. Adv Func Mater. 2014;24:7745-7753.

Kwok et al., Nanopore fabrication by controlled dielectric breakdown. PLoS One. Mar. 21, 2014;9(3):e92880. doi:10.1371/journal.pone.0092880. eCollection 2014.

Langecker et al., Synthetic lipid membrane channels formed by designed DNA nanostructures. Science. Nov. 16, 2012;338(6109):932-6. doi: 10.1126/science.1225624.

Larkin et al., Slow DNA transport through nanopores in hafnium oxide membranes. ACS Nano. Nov. 26, 2013;7(11):10121-10128. doi: 10.1021/nn404326f. Epub Oct. 4, 2013.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Oliver et al., Two breakdown mechanisms in ultrathin alumina barrier magnetic tunnel junctions. J Appl Phys. Feb. 1, 2004;95(3):1315-1322.

Shim et al., Electron beam induced local crystallization of HfO2 nanopores for biosensing applications. Nanoscale. Nov. 21, 2013;5(22):10887-93. doi: 10.1039/c3nr02608f. Epub Aug. 15, 2013.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Nucleobase recognition in ssDNA at the central constriction of the alpha-hemolysin pore. Nano Lett. Sep. 8, 2010;10(9):3633-7. doi: 10.1021/nl101955a.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Tahvildari et al., Integrating nanopore sensors within microfluidic channel arrays using controlled breakdown. Lab Chip. Mar. 21, 2015;15(6):1407-11. doi: 10.1039/c41c01366b. Supplementary Information.

Xie et al., Local electrical potential detection of DNA by nanowire-nanopore sensors. Nat Nanotechnol. Dec. 11, 2011;7(2):119-25. doi: 10.1038/nnano.2011.217.

Yanagi et al., Fabricating nanopores with diameters of sub-1 nm to 3 nm using multilevel pulse-voltage injection. Sci Rep. May 21, 2014;4:5000. doi: 10.1038/srep05000.

\* cited by examiner

METHODS AND APPARATUS FOR FORMING APERTURES IN A SOLID STATE MEMBRANE USING DIELECTRIC BREAKDOWN

RELATED APPLICATIONS

This application is a national stage application under U.S.C. § 371 of PCT International Application No. PCT/US2016/033487, filed May 20, 2016, which claims foreign priority benefits under 35 U.S.C. § 119(a)-(d) or 35 U.S.C. § 365(b) of British application number 1508669.7, filed May 20, 2015, the contents of each of which are incorporated herein by reference in their entireties.

The invention relates to a method and apparatus for forming single or multiple apertures in a solid state membrane using dielectric breakdown. The apertures may be nanoscale apertures, which may be referred to as nanopores, each having dimensions at the nanometre scale, for example a length and/or diameter of less than about 100 nm. The resultant porous membrane may be used in a wide number of applications.

Nanopores may be used in various devices where operations at the nanoscale are required. One important application is in localising, detecting and/or characterising molecules such as polynucleotides or polypeptides. Nanopore filters and nanoscale porous membranes are likewise important for many critical biological separation and characterization procedures, as well as filtration processes. Many other micro-fluidic and nano-fluidic processing and control applications similarly rely on nanoscale features in nanometric materials.

To produce a nanoscale structure such as a nanopore in a nanometrically-thin material, it is in general required to manipulate with the precision of single atoms. This is in contrast to most conventional microelectronic fabrication processes, which characteristically only require precision down to 10s of nanometres. Without feature resolution and fabrication precision at the atomic level, it is challenging to manipulate nanometrically-thin materials in a manner that exploits the particular characteristics which emerge at the nanoscale. Numerous methods for preparing nanopores in solid state membranes have been proposed, such as for example the methods disclosed in WO03003446 A3.

High precision nanoscale processing has historically required a one-at-a-time fabrication paradigm that is often costly and inefficient. Generally, the high-volume, batch fabrication techniques of conventional microelectronic production have been incompatible with nanoscale feature production and material manipulation. This has impeded commercial implementation of many important nanoscale applications.

Dielectric breakdown has been explored as an alternative approach for forming nanoscale apertures. However, controlling the dielectric process has been found to be challenging. Individual electronic control of the breakdown process for each aperture was found to be necessary to avoid damage to the membrane in which the apertures were formed and/or to achieve a desired aperture size. Forming apertures in thicker membranes was difficult because larger voltages were necessary. Larger voltages increase the risk of damage to the membrane or the formation of irregular apertures. Apertures of a precise desired size between a given solution chamber could only be produced one at a time, unless complex microfluidic arrangements were provided for forming multiple, mutually isolated fluid chambers at different positions, limiting the possibilities of commercial application.

It is an object of the invention to provide methods and apparatus which allow single or multiple apertures to be formed quickly and cheaply in a solid state membrane, particularly at the nanoscale.

According to an aspect of the invention, there is provided a method of forming a plurality of apertures in a solid state membrane using dielectric breakdown, wherein the membrane comprises a first surface area portion on one side of the membrane and a second surface area portion on the other side of the membrane, and each of a plurality of target regions comprises a recess or fluidic passage in the membrane that opens out into the first or second surface area portion, the method comprising: contacting all of the first surface area portion of the membrane with a first bath comprising ionic solution and all of the second surface area portion with a second bath comprising ionic solution; and applying a voltage across the membrane via first and second electrodes in respective contact with the first and second baths comprising ionic solutions to form an aperture at each of a plurality of the target regions in the membrane. The first and second baths may comprise different ions from each other. The ionic strength of the two baths may differ. As an alternative to the provision of an ionic solution, the first and/or second bath may comprise an ionic liquid.

Thus, a method is provided in which multiple apertures can be formed in parallel using dielectric breakdown. In an embodiment, at least 10 apertures are formed in parallel, optionally at least 50, optionally at least 100, optionally at least 1000, optionally at least 10000, optionally at least 100000, optionally at least 1000000. A continuous body of the ionic solution is brought into contact simultaneously with a plurality of target regions. The electrodes allow a potential difference to be applied across all of the target regions simultaneously. Dielectric breakdown and the formation of apertures occurs in parallel, thereby allowing a large number of apertures to be formed in the same amount of time as would be required for a single aperture. A large number of apertures can therefore be produced efficiently.

In an embodiment the method is applied in such a way that a single aperture is formed in each of the target regions. This may be achieved for example using suitably shaped and/or dimensioned and/or spatially distributed recesses or fluidic passages. For example, the apparatus may be arranged so that when dielectric breakdown occurs in one of the target regions the resulting reduction in electrical resistance through the membrane in the target region (due to the new electrical path provided by the aperture) does not prevent dielectric breakdown occurring in neighbouring target regions (e.g. by positioning the neighbouring target regions sufficiently far away).

Each of the target regions comprises a region where the thickness of membrane material separating the first bath from the second bath is thinner than elsewhere (so as to favour dielectric breakdown in that particular region relative to other regions). Where this thinning is provided by a recess or fluidic passage, the average depth of the recess or fluidic passage will typically be at least 10% less and may be at least 20%, 30%, 40%, 50%, 60%, 70%, 80%, 90%, 95% or 99% less than an average thickness of the membrane in regions where recesses or fluidic passages are not present. In one particular embodiment the thickness in the recess or fluidic passage is about 5-6 nm and the thickness in regions outside of the recess or fluidic passage is about 50-60 nm. In other embodiments the thickness in the recess or fluidic passage may be as small as about 2-3 nm. In an embodiment a fluidic passage is formed in a membrane having a thickness of more than 300 nm. Arranging for the thickness in a recess or fluidic passage to be about 2-3 nm in such an embodiment would result in an average depth in the recess or fluidic passage being at least 99% less than an average thickness of the membrane in regions where recesses or fluidic passages are not present.

In an embodiment, the aperture in each target region is grown until a diameter of the aperture is equal to or greater than a minimum thickness of membrane material separating the first bath from the second bath in the target region. The minimum thickness may be the thickness at the bottom of a recess or the thickness at the end of a fluidic passage. The inventors have recognised that a rate of growth of the aperture reduces suddenly when the diameter of the aperture is equal to or slightly greater than a thickness of membrane material (typically between about 1 and 1.5 times the thickness of the membrane material) in which the aperture is being formed. This is because the access resistance becomes significant when the aperture diameter is comparable to the aperture thickness, which results in the voltage drop across the aperture being reduced. In other words, the access resistance acts as a limiting resistor. By deliberately growing the aperture until this point is reached it is possible to control the diameter of the aperture accurately without sophisticated electronics. In particular, it is possible simultaneously to form multiple apertures of the same size, even where those apertures may have started growing at slightly different times and/or have undergone slightly different growth rates (due to the stochastic nature of the dielectric breakdown process). When the diameters of some of the apertures become equal to or greater than the thickness of the membrane material where they are formed, the other apertures will quickly catch up, thereby leading to a highly uniform size distribution (for example such that a diameter variation between different pores is within about 10-20% or better). This approach, based on using the thickness of the membrane material to control aperture size, allows accurate control of aperture size because modern fabrication processes can control the thickness of the membrane material (i.e. during formation of the recesses or fluidic passages) with high accuracy. For example thickness accuracy down to 1 nm or even sub nm is realistic, whereas the accuracy with which features can be formed in directions perpendicular to the depth using standard lithographic processes is typically of the order of 10s of nm.

The diameter of the apertures that may be produced using the method of the invention may range from 0.1 nm to 100 nm, such as from 1.0 nm to 10 nm. Apertures of 0.5 nm, 0.6 nm, 0.7 nm, 0.8 nm, 0.9 nm, 1.5 nm, 2 nm, 3 nm, 4 nm or 5 nm may be produced. The distance (pitch) between the apertures may be 10 nm or more, optionally 50 nm or more, optionally 100 nm or more, optionally 1 micron or more, optionally 50 microns or more depending upon the application. The apertures may be provided in a regular array, for example a square or hexagonal packed array, or an irregular array. For example, a square packed array with apertures having a diameter of 2 nm and a separation between the apertures of 20 nm, the density of the apertures in the array is $1/121$ nm$^2$.

In an embodiment, the thickness of the membrane material at the bottom of recesses or at the end of fluidic passages is controlled by forming the membrane from a plurality of different layers (e.g. two layers) and using the interface between two of the layers to define a boundary of the recess or fluidic passage (e.g. the bottom or end, respectively), e.g. by arranging for an etching process to slow down or stop at or near (e.g. just beyond) the interface. Arranging for the etching process to slow down or stop at or near the interface can be achieved by selecting the compositions of the layers and the nature of the etching process (e.g. etchant composition) such that the etching process proceeds quickly for one of the layers and slowly or not at all for the other layer.

In an embodiment one or more of the target regions comprises a fluidic passage and one or more of the fluidic passages has an aspect ratio of greater than 1, optionally greater than 5, optionally greater than 10, optionally greater than 20, optionally greater than 30, optionally greater than 40, optionally greater than 50, optionally greater than 75, optionally greater than 100. The aspect ratio is defined as a ratio of a length of the fluidic passage to an average width of the fluidic passage. Fluidic passages having a high aspect ratio will typically have a fluidic electrical resistance that is higher than fluidic passages having a lower aspect ratio. Such fluidic passages can act as current limiting resistors, reducing the voltage across the membrane significantly when the aperture is formed. The voltage will be reduced by approximately $R_2/(R_1+R_2)$ where $R_2$ is the resistance of the fluidic passage, and $R_1$ is the resistance of the aperture. This expression does not take into account the effects of access resistance or fully account for regions where the electrical field lines change direction. A more accurate description of the voltage reduction, with access resistance included, is given by the following expression:

$$(R_2+R_{a(2)})/(2R_{a(1)}+R_1+R_2+R_{a(2)})$$

where $R_{a(n)}=\rho_n/2d_n$ is the access resistance (for the aperture when n=1 and for the fluidic passage when n=2), $\rho_n$ is the resistivity of the ionic solution on the respective side of the membrane, and $d_1$, $d_2$ are the diameters of the aperture and the fluidic passage respectively. This calculation assumes that $d_2 \gg d_1$. Otherwise, the resistance of the region around the interface between the aperture and the fluidic passage needs to be modelled in more detail. It is possible to account for changes in electric field line direction using finite element simulation.

In an embodiment, one or more of the target regions comprises a fluidic passage and in each of one or more of the fluidic passages an aperture is formed which has a fluidic electrical resistance of less than 10 times the fluidic electrical resistance of the fluidic passage, optionally less than 5 times, optionally less than 2 times. In an embodiment, one or more of the target regions comprises a fluidic passage and in each of one or more of the fluidic passages an aperture is formed which has a fluidic electrical resistance that is less than the fluidic electrical resistance of the fluidic passage. Arranging for the fluidic electrical resistance of a fluidic passage to be a least a significant portion (e.g. between about 0.3 and 0.5) of the fluidic electrical resistance of the aperture in this manner ensures that after aperture formation there is a significant voltage drop along the length of the fluidic resistor, reducing the voltage drop across the membrane material in the region of the aperture. Furthermore, providing fluidic passages having a significant fluidic electrical resistance reduces the effect of the formation of an aperture in one fluidic passage on the electrical field in any neighbouring fluidic passage. Even in a case where an erroneously large aperture is formed in one fluidic passage, the fluidic electrical resistance of the fluidic passage itself will prevent any excessive reduction in the electrical field in neighbouring fluidic passages, such that apertures can still be correctly formed in those passages.

In an embodiment, fluidic passages having different fluidic electrical resistances are provided in different target regions, and a corresponding plurality of differently sized apertures are grown in parallel via the voltage applied via the first and second electrodes. This allows efficient formation of multiple apertures of different size in a controlled manner. In this embodiment, the reduction in voltage across the aperture after the aperture has been formed will be different for each of the fluidic passages having a different fluidic electrical resistance. The subsequent rate of growth of the apertures will thus be different. This can be exploited to enable simultaneous formation of apertures of different size, even if the thickness of the membrane material at the end of the fluidic passages is the same. The size of aperture at which the rate of growth slows markedly will be different for each of the fluidic passages having a different fluidic electrical resistance.

In an alternative aspect of the invention, there is provided a method of forming an aperture in a solid state membrane using dielectric breakdown, wherein the membrane comprises a first surface area portion on one side of the membrane and a second surface area portion on the other side of the membrane, comprising: contacting the first surface area portion of the membrane with a first bath comprising ionic solution and the second surface area portion with a second bath comprising ionic solution; and applying a voltage across the membrane via first and second electrodes in respective contact with the first and second baths comprising ionic solutions to form an aperture in the membrane, wherein a current limiting resistor is provided in series between the membrane and the first or second electrode, the current limiting resistor having an electrical resistances which is at least 10% as high as an electrical resistance of the aperture at any time after formation of the aperture, optionally at least 20%, optionally at least 50%, optionally at least 100%.

The current limiting resistor provides a resistance that is in addition to the access resistance associated with the ionic solutions in the first and second baths when the current limiting resistor is not present. The current limiting resistor increases an amount of reduction of voltage across the aperture when the aperture is formed, relative to a case where the current limiting resistor is not provided. The current limiting resistor may comprise either or both of a fluidic resistor provided in the first or second bath and an external resistor that is provided at least partially outside of the first and second baths. The external resistor may be a conventional resistor of the passive solid state type which is routinely used in electrical circuits not involving fluids.

The current limiting resistor provides a simple way of controlling the rate of the aperture diameter growth process without sophisticated and expensive electronics. The current limiting resistor determines the eventual aperture diameter at a given applied voltage. The approach is simpler for example than prior art alternatives in which electronic feedback is used to cut off the voltage when dielectric breakdown begins, or in which very short voltage pulses are used to allow the voltage to be stopped quickly enough. The method may nonetheless comprise the use of electronic feedback to indicate the formation of the apertures, for example by measurement of the change in ion current flowing through the apertures between the electrodes. The feedback may be operative for example to limit the number of apertures formed, for example by switching off the dielectric breakdown process after a particular value of ion current has been exceeded.

In an alternative aspect, there is provided a method of forming an aperture in a solid state membrane using dielectric breakdown, the method comprising: applying a voltage across the membrane to form the aperture using dielectric breakdown, wherein: the membrane comprises a plurality of sub-layers; at least two of the sub-layers have a different composition relative to each other; and each of the sub-layers is formed by atomic layer deposition.

The inventors have found that forming the membrane from multiple sub-layers of different composition using atomic layer deposition makes it possible to control the geometry of apertures with high accuracy, even where the membrane is extremely thin. Atomic layer deposition allows very uniform and precise thickness control at resolutions of the order of ~1 Å. Materials which are inert to many reactive ion etch (RIE) processes can be applied using atomic layer deposition. The level of control provided by atomic layer deposition is higher than can be achieved typically using alternative film growth techniques. The length of the aperture, which is dictated by the thickness of the layer or layers in which the aperture is formed, can be controlled with high accuracy.

Where the aperture is used for sensing a molecular entity (e.g. DNA material) passing through the aperture, performance (e.g. the ability to distinguish between different DNA bases) has been found to depend critically on the diameter and length of the aperture. Improving the accuracy with which the diameter and/or length can be controlled improves performance The inventors have furthermore found that forming the membrane from multiple sub-layers of different composition using atomic layer deposition provides an aperture that is highly stable during use. For example, the diameters and lengths of apertures formed in this way have been found to remain stable over long periods of time (e.g. several weeks or over a month) during use. In an embodiment, the plurality of sub-layers comprises a sequence of sub-layers that repeats a plurality of times, each repeating sequence comprising at least a first sub-layer and a second sub-layer directly adjacent to the first sub-layer, preferably with the first sub-layers being non-epitaxial with respect to the second sub-layers. The use of such a repeating sequence of non-epitaxial sub-layers reduces the formation of defects due to crystal growth within the sub-layers, preserving an amorphous film. The quality of the sub-layers, and the quality and integrity of the overall membrane, is thereby improved, by improving uniformity and/or reducing defect concentration.

In an embodiment, the plurality of sub-layers is annealed prior to formation of the aperture. The anneal may be performed below a temperature at which significant crystallization in the sub-layers might occur. Alternatively, the anneal may be performed at higher temperatures. The anneal improves the quality of the sub-layers (e.g. improving uniformity and/or reducing defect concentration).

Improving the quality of the sub-layers reduces electrical leakage through the sub-layers, which could otherwise disrupt optimal formation of apertures using dielectric breakdown.

In an alternative aspect, there is provided an apparatus for forming a plurality of apertures in a solid state membrane using dielectric breakdown, comprising: a first bath configured to hold an ionic solution in contact with all of a first surface area portion on one side of a solid state membrane; a second bath configured to hold an ionic solution in contact with all of a second surface area portion on the other side of the membrane; and a voltage applicator comprising a first electrode configured to contact the ionic solution in the first bath and a second electrode configured to contact the ionic solution in the second bath, wherein the membrane comprises a plurality of target regions, each target region comprising a recess or fluidic passage in the membrane that opens out into the first or second surface area portion; and the target regions are configured such that a voltage applied via the first and second electrodes can cause formation of a single aperture in each of the target regions.

In an alternative aspect, there is provided an apparatus for forming an aperture in a solid state membrane using dielectric breakdown, comprising: a first bath holding an ionic solution in contact with a first surface area portion on one side of a solid state membrane; a second bath holding an ionic solution in contact with a second surface area portion on the other side of the membrane; and a voltage applicator comprising a first electrode configured to contact the ionic solution in the first bath and a second electrode configured to contact the ionic solution in the second bath, wherein a current limiting resistor is provided in series between the membrane and the first or second electrode, the current limiting resistor having an electrical resistance which is at least 10% as high as an electrical resistance of the aperture at any time after formation of the aperture.

In an alternative aspect, there is provided an apparatus for forming an aperture in a solid state membrane using dielectric breakdown, comprising: a bath system for holding an ionic solution in contact with each side of the solid state membrane; and a voltage applicator for applying a voltage across the membrane via the ionic solution in order to form the aperture in the membrane using dielectric breakdown, wherein: the membrane comprises a plurality of sub-layers; at least two of the sub-layers have a different composition relative to each other; and each of the sub-layers is formed by atomic layer deposition.

In an alternative aspect, there is provided a solid state membrane comprising a plurality of apertures, each aperture having a diameter equal to or greater than a minimum thickness of membrane material separating the first bath from the second bath where the aperture is formed.

In an alternative aspect, there is provided a solid state membrane comprising: a plurality of target regions, each target region comprising a recess or fluidic passage in the membrane; and a plurality of nanoscale apertures, each aperture being located within a different one of the target regions and having a diameter that is equal to or greater than a minimum thickness of the target region.

Embodiments of the invention will now be described, by way of example only, with reference to the accompanying drawings in which corresponding reference symbols indicate corresponding parts, and in which.

Figure 11:
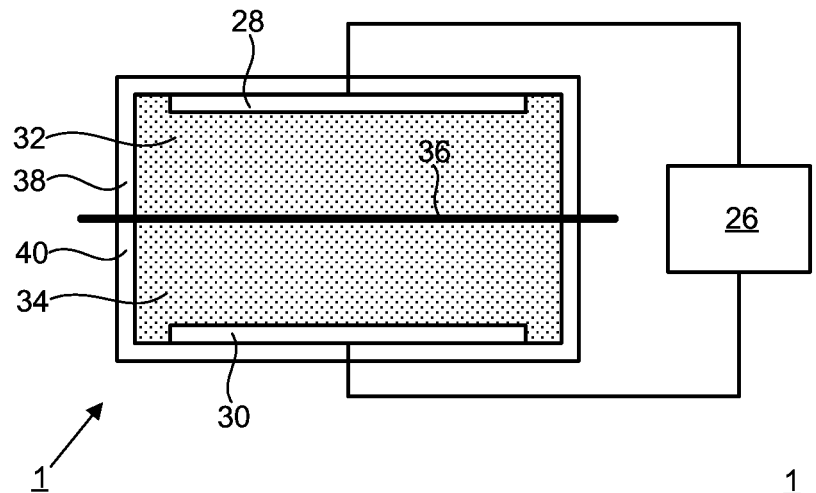
FIG. 11 depicts an example apparatus for forming a plurality of nanoscale apertures.

In an embodiment, an example of which is shown in FIG. 11, there is provided an apparatus 1 for forming a plurality of apertures in a membrane. The apertures are formed by dielectric breakdown of the membrane. In an embodiment the membrane is a solid state membrane. In an embodiment the apertures are nanoscale apertures, for example apertures having a characteristic dimension (e.g. diameter or depth or both) of the order of 100 nm or less, optionally 50 nm or less, optionally 20 nm or less, optionally 10 nm or less, optionally 5 nm or less, optionally 2 nm or less, optionally 1 nm or less. Each aperture provides a conduit extending from one side of the membrane to the other side of the membrane, thereby fully traversing the membrane.

Figure 1:
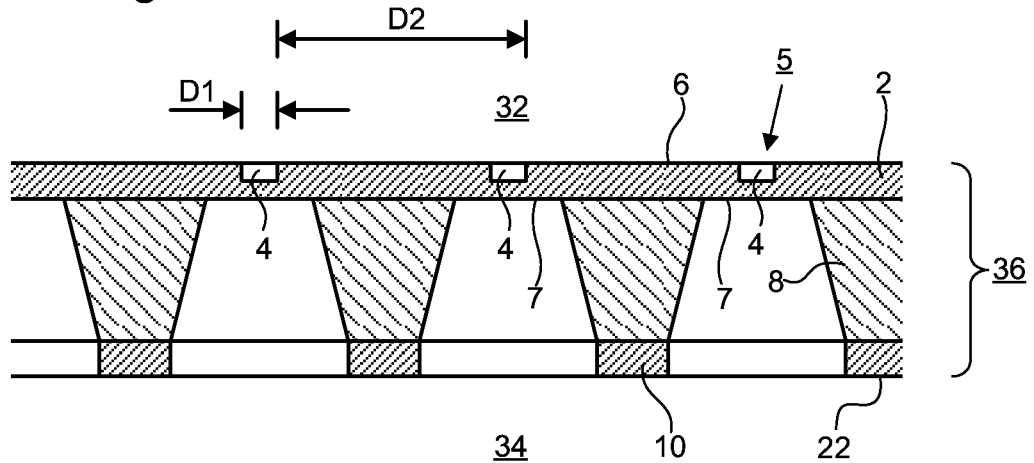
FIG. 1 is a schematic side sectional view of a portion of a membrane assembly comprising a membrane with a plurality of recesses in corresponding target regions.

FIG. 1 depicts an example configuration for the membrane 2. In this embodiment the membrane 2 is attached to a support structure 8,10. The combination of the membrane 2 and support structure 8,10 may be referred to as a membrane assembly 36. The membrane assembly 36 may be formed by manufacturing a plurality of membrane assemblies using a single integral membrane 2 (e.g. a wafer) and cutting out the membrane assembly 36 from the plurality of membrane assemblies. Alternatively, the plurality of membrane assemblies may remain connected together with the apparatus 1 being configured to interact with just one of the membrane assemblies. In such an embodiment, other instances of the apparatus 1 may be provided to interact with other ones of the membrane assemblies. Alternatively, the membrane assembly 36 may comprise the whole of a wafer forming the membrane 2.

The membrane 2 may be composed from various materials and combinations of materials. The resistivity of the membrane 2 should be sufficiently high to allow dielectric breakdown to occur. If the resistivity is anisotropic, it should be sufficiently high in the direction perpendicular to the membrane surfaces 6, 7 to allow dielectric breakdown to occur. The membrane 2 may comprise a single layer or a plurality of different layers. Specific examples of membranes having plural layers, and their associated advantages, are discussed below with reference to FIGS. 16-19.

As shown for example in FIGS. 1 and 11, the apparatus 1 comprises a first bath 38 configured to hold an ionic solution 32. The ionic solution 32 in the first bath 38 contacts all of a first surface area portion 6 on one side of the membrane 2 (the upper side of the membrane 2 in the orientation shown in the figures). The apparatus 1 further comprises a second bath 40 configured to hold an ionic solution 34. The composition of the ionic solution 34 in the second bath 40 may be the same as or different from the composition of the ionic solution 32 in the first bath 38. The ionic solution 34 in the second bath 40 contacts all of a second surface area portion 7 on the other side of the membrane 2 (the lower side of the membrane 2 in the orientation shown in the figures). The combination of the first bath 38 and the second bath 40 may be referred to as a bath system. Either or both of the first and second surface area portions 6,7 may or may not be formed from multiple regions, or islands, that are isolated from each other. The contacting of all of each of the first and second surface area portions 6,7 by an ionic solutions means that all portions of each of the first and second surface area portions 6,7 are connected together by a continuous body of the ionic solution. A voltage applied to ionic solution in contact with the first surface area portion 6 will therefore be applied to all of the first surface area portion 6. A voltage applied to ionic solution in contact with the second surface area portion 7 will be applied to all of the second surface area portion 7.

A voltage applicator is provided for applying a voltage across the membrane 2, including in target regions 5. The voltage is applied via the ionic solution 32,34 and the first and second surface area portions 6,7 of the membrane 2. The voltage applicator comprises a first electrode 28 and a second electrode 30. The first electrode 28 is configured to contact the ionic solution 32 in the first bath 38. The second electrode 30 is configured to contact the ionic solution 34 in the second bath 40. In an embodiment, the voltage applicator comprises a controller 26 for controlling the voltage applied by the voltage applicator.

The membrane 2 comprises a plurality of the target regions 5. Each of the target regions 5 comprises a recess 4 or fluidic passage 24. The recess 4 or fluidic passage 24 opens out into the first or second surface area portion 6,7. The recess 4 or fluidic passage 24 provides a path of reduced thickness between the first and second baths, thereby favouring initiation of aperture formation in the target region 5. For example, a region of the membrane 2 at the base of a recess 4 or at the end of a fluidic passage 24 may be thinner than in regions outside of the target region 5.

The apparatus 1 is configured such that a voltage applied via the first and second electrodes 28,30 can cause formation of a single aperture 20 in each of the target regions 5. Thus, for example, the target regions 5 are spaced apart from each sufficiently that the reduction in resistance that occurs when dielectric breakdown is initiated in one target region 5 does not prevent dielectric breakdown from being initiated in a neighbouring target region 5. This is important because although the voltage is applied simultaneously to all of the target regions 5, the exact moment when dielectric breakdown begins may vary significantly between different target regions. The reduction in resistance will tend to reduce the magnitude of the electric field in the region of the target region 5.

Figure 2:
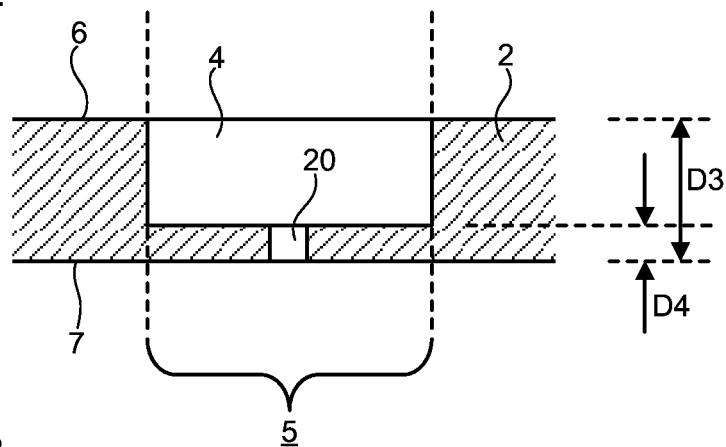
FIG. 2 is a magnified side sectional view of one of the recesses in the membrane of FIG. 1, having a rectangular depth profile.

In the example arrangement shown in FIG. 1, the membrane 2 comprises a layer of SiNx. The membrane 2 is supported by a layer 8 of Si and a further layer 10 of SiNx (such that the Si layer 8 is sandwiched between the SiNx of the membrane 2 and the SiNx of the layer 10). In the example shown, the Si layer 8 has a thickness of about 300 microns. The SiNx membrane 2 and layer 10 each have a thickness D3 of about 40 nm. The membrane assembly 36 may be formed as follows. Conventional lithography and a KOH etch can be used to form the membrane 2 and layers 8 and 10. In this particular embodiment each of the target areas 5 comprises a recess 4 opening out into an upper surface of the membrane 2. E-beam lithography and a reactive ion etch may be used to define areas (of any shape, for example circular) defining these recesses 4 and to thin down the membrane 2 in these areas to provide the required depth of recess 4. FIG. 2 provides a magnified view of one of the recesses 4 of FIG. 1. The thickness D4 of the membrane 2 in the recess 4 in this example is about 10 nm (meaning that the depth of the recess 4 is about 30 nm).

Figure 7:
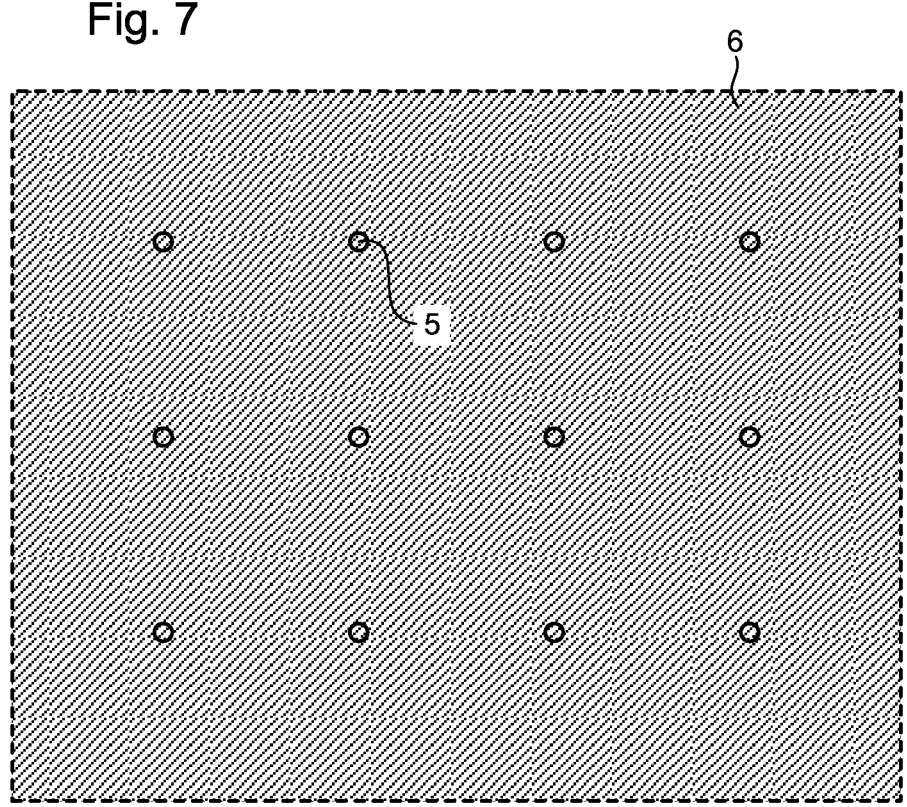
FIG. 7 is a top plan view of a portion of an example membrane showing a plurality of target regions formed in a first surface area portion to be contacted by an ionic solution.
Figure 8:
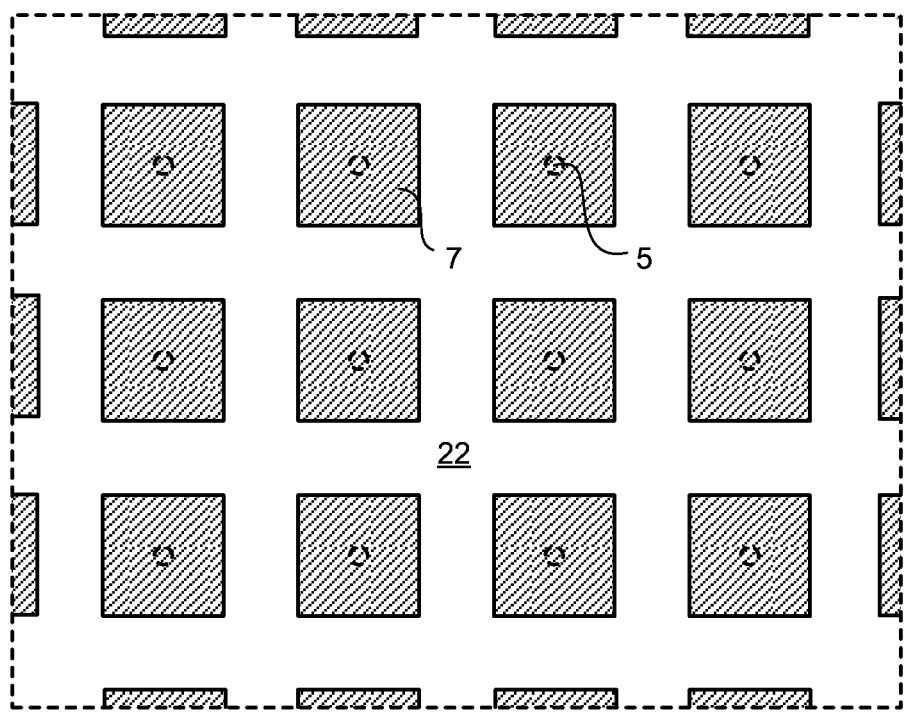
FIG. 8 is a bottom plan view of a portion of the membrane of FIG. 7, showing a second surface area portion to be contacted by an ionic solution, each isolated region of the second surface area portion containing a single target region.

FIGS. 7 and 8 are top and bottom plan views respectively of a portion of the membrane 2 of FIG. 1. As can be seen, the first surface area portion 6 (FIG. 7) consists of a single area without any holes. The second surface area portion 7 comprises a plurality of isolated regions which are separated from each other by the layer 8 of the support structure. The white areas shown correspond to a bottom surface 22 of layer 10 of the support structure. In this example, the isolated regions of the second surface area portion 7 are square with dimensions 15×15 microns. The shape of the isolated regions is determined by the particular process chosen for fabrication. KOH etch produces square shape etch pits but reactive ion etch could take any other shape, for example, circular shape (e.g. with diameter of 15 microns).

Figure 9:
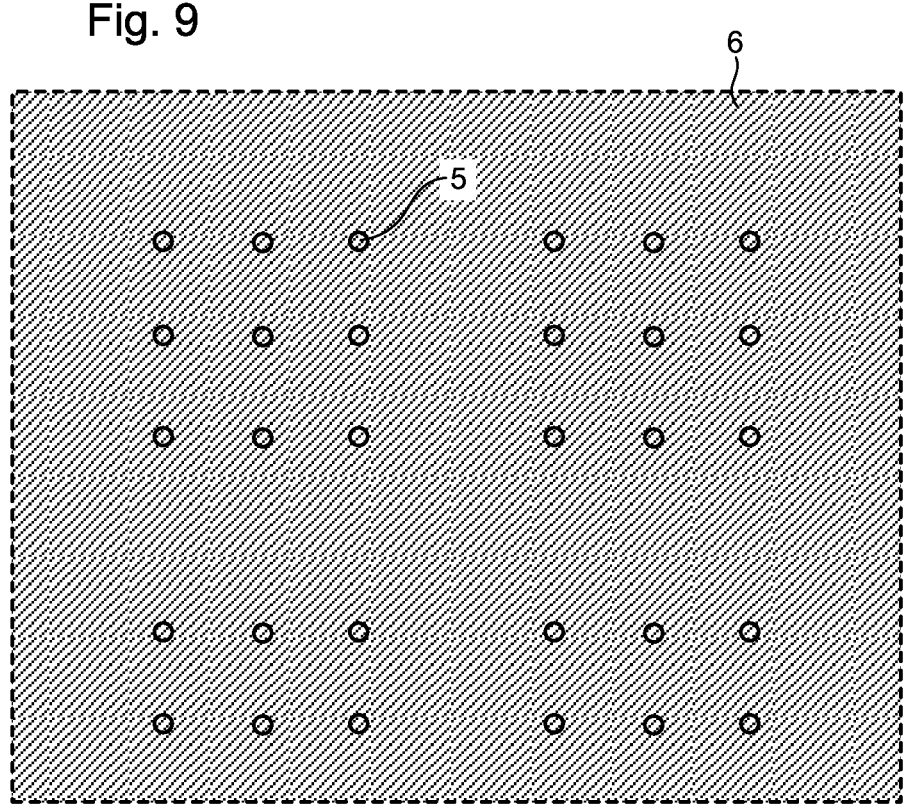
FIG. 9 is a top plan view of a portion of an alternative example membrane showing a plurality of target regions formed in a first surface area portion to be contacted by an ionic solution.
Figure 10:
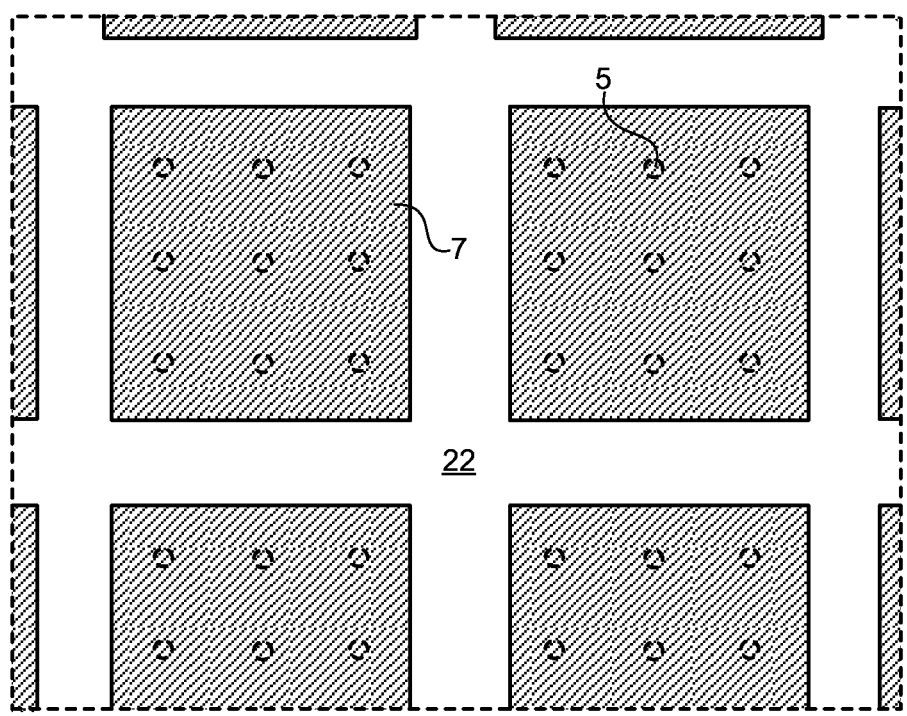
FIG. 10 is a bottom plan view of a portion of the membrane of FIG. 9, showing a second surface area portion to be contacted by an ionic solution, each isolated region of the second surface area portion containing plural target regions.

In the examples of FIGS. 1, 7 and 8, each of the isolated regions in the second surface area portion 7 contains one target region 5 (comprising a recess 4 formed in the upper side of the membrane 2). In this example the target regions 5 are therefore spaced relatively far apart from each other (greater than about 15 microns). However, this is not essential. In other embodiments, as shown for example in FIGS. 9 and 10, each of the isolated regions in the second surface area portion 7 contain multiple target regions 5 and/or the target regions 5 are otherwise positioned closer to each other than is the case in FIGS. 1, 7 and 8. Examples of a portion of a membrane 2 having a plurality of more closely spaced target regions 5 are shown schematically in FIGS. 4-6. In such examples, the target regions 5 may have a diameter D1 of about 50 nm and a separation D2 of about 1 micron for example. Various other dimensions and spacings may be chosen according to requirements. In an embodiment, a single isolated region is provided and the single isolated region comprises multiple target regions.

Figure 3:
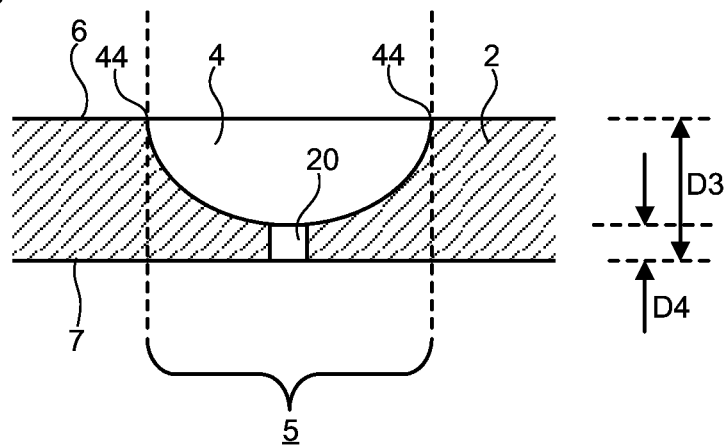
FIG. 3 is a magnified side sectional view of an alternative recess having a curved depth profile.

The shape in plan view of the recesses 4 or fluidic passages 24 may take any form, for example circular. In the embodiment described with reference to FIGS. 1, 2 and 4, the recesses 4 have a circular shape in plan view and a rectangular depth profile (thereby forming a cylinder). In other embodiments, the recesses 4 or fluidic passages 24 may have different profiles. In one embodiment, as shown in FIGS. 3 and 5 for recesses 4, the recesses 4 or fluidic passages 24 have a depth profile in which the depth increases progressively from an edge 44 of an opening of the recess 4 or fluidic passage 24 towards a central region (e.g. axially central in the case of a fluidic passage 44) of the recess 4 or fluidic passage 24, prior to a formation of any aperture 20 in the recess 4 or fluidic passage 24. The depth profile may be a smooth depth profile, for example a rounded depth profile, as shown in FIGS. 3 and 5. This may be formed for example by suitable control of a reactive ion etch or by using a wet etch process. Alternatively the depth profile may be angular, e.g. conical. The area of the thinnest portion of the membrane 2 in plan view in a recess 4 or fluidic passage 24 of this type is significantly smaller than the area in plan view of the whole of the recess 4 or fluidic passage 24 as defined by the edge 44, optionally at least 75% smaller, optionally at least 90% smaller, optionally at least 95% smaller. The area in which dielectric breakdown will be most favoured (i.e. the thinnest region) may therefore be smaller in such a recess 4 or fluidic passage 24 than in other embodiments, for example as in the recesses 4 shown in FIGS. 1, 2 and 4. The likelihood of more than one separate aperture forming in the same recess 4 or fluidic passage 24 is therefore reduced because there is less space available for such a process to occur. The formation of an aperture in each recess 4 or fluidic passage 24 can therefore be simplified and/or made more reliable. For example, as described in detail above, a repeated application of first and second voltages is not necessary to form the apertures reliably. All of the apertures can for example be formed by constantly applying a voltage at a level (e.g. 10V) which is higher than a chosen percentile or an upper limit of the statistical distribution of minimum voltages required for initiating an aperture 20.

The fluidic passages 24 may extend perpendicularly to the plane of the membrane 2 and/or in a straight line, for example forming cylindrical shapes. However, this is not essential. A fluidic passages 24 may take various other forms, having for example at least a portion which does not extend in a straight line and/or which does not extend in a direction perpendicular to the plane of the membrane 2. Serpentine shapes and shapes in which the fluidic passage 24 has a portion extending parallel to the plane of the membrane 2 can be provided for example. Such shapes may be useful where it is desired to provide a fluidic passage 24 with a high aspect ratio in order to provide a high fluidic electrical resistance.

In an embodiment, fluidic passages 24 are provided which have an aspect ratio of greater than 1, optionally much greater than 1. The aspect ratio is defined as a ratio of a length of the fluidic passage to an average width of the fluidic passage. FIG. 6 shows an example of a portion of a membrane 2 corresponding to that of FIGS. 4 and 5 except that a plurality of fluidic passages 24 having an aspect ratio greater than 1 are provided instead of relatively shallow recesses 4. The role of fluidic passages 24 as current limiting resistors is discussed in further detail below.

In an embodiment, a voltage is applied across the membrane 2 until a plurality of apertures 20 have been formed which are spatially separated from each other. In an embodiment, a single aperture 20 is formed in each and every one of the target regions 5. Each aperture 20 is formed in a recess 4 or fluidic passage 24.

In an embodiment, the aperture 20 in each target region 5 is grown (by continuing to apply the voltage) until a diameter of the aperture 20 is equal to or greater than a minimum thickness of membrane material separating the first bath from the second bath in the target region 5. Where a fluidic passage 24 is provided the minimum thickness may be the thickness of the membrane material at the end of the fluidic passage 24. This may not be equal to the overall membrane thickness 2 for some geometries, for example geometries in which the fluidic passage 24 does not extend exclusively in a direction perpendicular to the plane of the membrane 2. Where a recess 4 is provided the minimum thickness will typically be the thickness at the base of the recess 4.

The inventors have recognised that the rate of growth of an aperture 20 in a membrane 2 reduces as the diameter of the aperture 20 increases. The growth rate drops to almost zero when the diameter of the aperture 20 is equal to or greater than the thickness of material in which the aperture 20 is being formed. The inventors have also recognised that this effect makes it possible to control the size of apertures 20 formed by dielectric breakdown in a simple and reliable manner. Instead of needing to form apertures 20 individually in series, with complex electronics to monitor the growth process, multiple apertures 20 can be formed simultaneously with little or no real time monitoring of the growth process. A single voltage can be applied simultaneously to multiple target regions 5. Dielectric breakdown may be initiated at slightly different times for different target regions 5, so that during the growth process apertures 20 of various different sizes may co-exist. However, when the growth process reaches the point where the diameters of larger individual apertures 20 become equal to or greater than the thickness of the material around the apertures 20, growth of those apertures 20 will slow significantly, allowing the smaller apertures 20 to catch up. If the process is continued until the diameters of all of the apertures 20 are equal to or greater than the thickness of the material around the apertures 20, it is found that the slowing of the growth process for the larger apertures 20 means that all of the apertures 20 have substantially the same size.

In an embodiment, a substantially constant uninterrupted voltage is applied for a majority of a time during which the aperture 20 is grown by the voltage. In an embodiment, applicable particularly where the target regions 5 comprise recesses 4 or fluid passages 24 that have a rectangular depth profile (e.g. cylindrical), a first voltage is applied that initiates aperture formation in the target regions 5. The first voltage may be applied for a relatively short time (e.g. 100 ms for a configuration for forming 10-20 nm apertures, such as that shown in FIG. 1). A second voltage, lower than the first voltage is applied after the first voltage for a longer time (e.g. 1 min for a configuration for forming 10-20 nm apertures, such as that shown in FIG. 1). In an embodiment the second voltage is lower than would be necessary to initiate formation of apertures in the same target regions. The second voltage is applied to grow the existing apertures 20 without generating any new apertures. In one example implementation a first voltage of about 10V was used to initiate the dielectric breakdown. A second voltage of about 9V was then used to grow the apertures 20. The process was continued until the current stabilized, indicating that diameters of the apertures 20 had reached the thickness of the material surrounding the apertures 20 and their growth had slowed.

In an embodiment, the sequence of the first and second voltages is applied a plurality of times. This may be necessary to ensure that apertures 20 are initiated in all of the target regions 5. The sequence of first and second voltages may be applied repeatedly until it is detected that the current across the membrane 2 is stable. The inventors found that applying this approach to the arrangement shown in FIG. 1, for example, can be used reliably to produce plural apertures 20 having a uniform diameter of 15 nm.

In an embodiment, a third voltage is applied after the first and second voltages. The third voltage is equal to or higher than the first voltage (e.g. 10V). The third voltage is applied for a longer time than either or both of the first and second voltages (e.g. 3 min). The third voltage acts to homogenize (make more uniform) the aperture diameters.

The repeated application of the first and second voltages is particularly desirable where there is a chance of more than one aperture being formed in any single one of the target regions 5, for example in a single recess 4 or fluidic resistor 24 in one of the target regions 5. This may be more likely for example where the thinnest portion of a target region 5 extends over a relatively large area, for example in recesses 4 having a rectangular depth profile (e.g. as in FIGS. 1, 2 and 4). For recesses 4 having a thinnest portion representing a smaller proportion of the target region 5 (e.g. as in FIGS. 3 and 5), the repeated application of the first and second voltages may not be necessary. In this situation, all of the apertures 20 may be formed by constantly applying a voltage at a level (e.g. 10V) which is higher than the minimum required for initiating an aperture 20.

In an embodiment, the aperture 20 in each target region 5 is grown until a diameter of the aperture 20 is in the range of 5 nm to 40 nm. However, apertures which are smaller than this range or larger than this range may also be formed according to requirements.

In an embodiment all of the recesses 4 or fluidic resistors 24 provided have the same geometry (e.g. depth, thickness profile, length, aspect ratio, thickness etc.). This may be appropriate where it is desired simultaneously to form identical apertures in each of the target regions 5.

In an embodiment one or more of the target regions 5 comprises a recess 4 having an average width less than 5 times an average depth. The inventors have found that keeping recesses 4 within this constraint greatly reduces the risk of more than one aperture 20 being initiated in the same recess 4.

The above described embodiments, and other embodiments, allow membranes 2 to be formed which comprise a plurality of apertures 20. The aperture diameter can be controlled by the thickness of the material in which the apertures are formed, for example by growing each aperture until its diameter is equal to or greater than a thickness of the membrane material separating the two baths in the region where the aperture is formed. Modern fabrication processes allow the membrane thickness to be controlled with very high precision (e.g. down to 1 nm or less), thereby allowing accurate control of the aperture diameter. It is not essential for each aperture to be grown until its diameter is equal to or greater than a thickness of the membrane 2 in the region where the aperture is formed. In other embodiments, apertures are formed that are smaller than this.

Relatively high voltages can be required to initiate the dielectric breakdown process. This is particularly the case where relatively large apertures (e.g. greater than about 30 nm) need to be formed, because this requires a thicker membrane in the target regions and, consequently, a higher voltage for breakdown. The sudden reduction in resistance that occurs when the dielectric breakdown first occurs can lead to a large current flowing through the baths 32 and 34 and newly formed aperture 20. The large current could in principle oxidise or reduce a species present in the ionic solution in the baths and/or lead to damage to, or unpredictable behaviour of, the aperture 20 itself. For example, in a 46 nm thick SiNx membrane with 100 nm diameter, 30 nm thick recesses, an applied voltage of 20-30V is required to initiate dielectric breakdown. The current driven through the system after dielectric breakdown can completely destroy the aperture 20.

Figure 12:
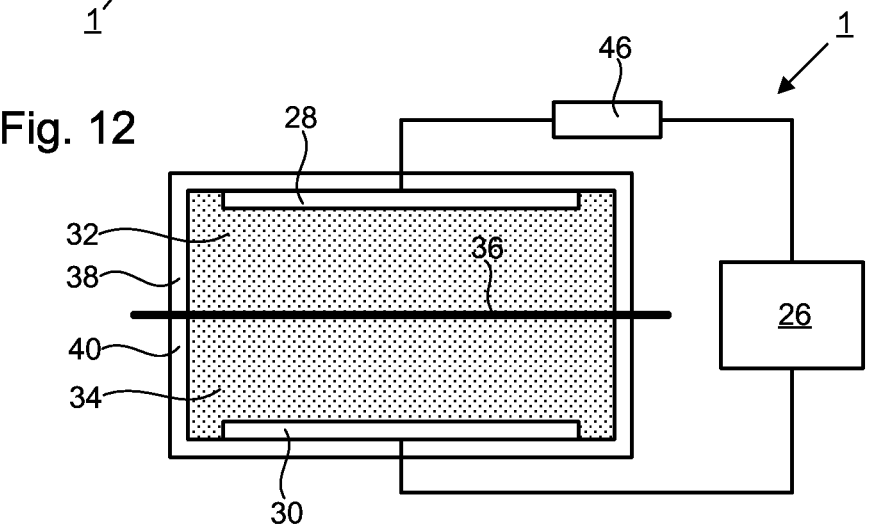
FIG. 12 depicts an alternative example apparatus for forming a nanoscale aperture in which an external resistor is provided as a current limiting resistor.

In an embodiment, an example of which is shown in FIG. 12, a current limiting resistor 46 is provided. The current limiting resistor provides a resistance that is additional to the access resistance provided through the ionic solution in the absence of the current limiting resistor 46. The current limiting resistor 46 is provided in series between the membrane 2 and the first or second electrode 28, 30. When the resistance across the membrane 2 suddenly falls when an aperture 20 is formed in the membrane 2, the current limiting resistor 46 limits the resulting increase in current flow through the aperture 20. The current limiting resistor 46 acts to reduce the voltage acting across the electrodes 28, 30 in proportion with the current flowing between them. In the absence of the current limiting resistor 46, the controller 26 will try to maintain a constant voltage between the electrodes 28,30, with the voltage across the newly formed aperture 20 only falling in that case with increasing current due to the potential drop across the ionic solution between the electrodes 28, 30 and the aperture 20, or because of overload of the power source being used by the controller 26. The current limiting resistor 46 therefore increases an amount of reduction of voltage across each aperture 20 when the aperture 20 is formed, relative to a case where the current limiting resistor 46 is not provided. In the example discussed above (46 nm thick SiNx membrane with 100 nm diameter, 30 nm thick recess), a current limiting resistor 46 of about 2MΩ was found to be suitable. More generally, the current limiting resistor should have an electrical resistance which is at least 10% as high as an electrical resistance of the aperture (i.e. a fluidic electrical resistance of the aperture) at any time after formation of the aperture 20 (i.e. after the aperture 20 is fully formed, rather than during an intermediate transient phase immediately after dielectric breakdown first takes place). Typically, the current limiting resistor is chosen to have an electrical resistance that is of a similar order of magnitude to the fluidic electrical resistance of the aperture 20, so that a significant drop in the potential difference across the membrane at the aperture 20 occurs when the aperture 20 is formed.

Figure 13:
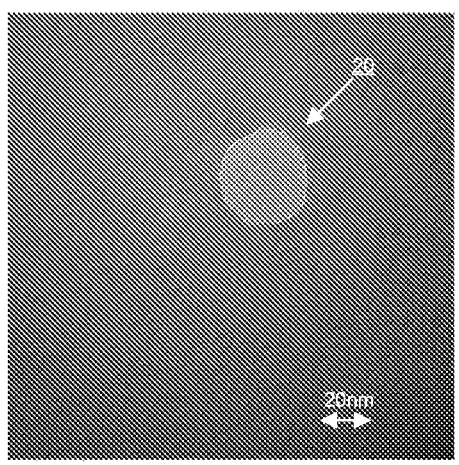
FIG. 13 is a TEM image of an example aperture.

The current limiting resistor 46 also reduces the rate of growth of the aperture 20 for a constant applied voltage. The rate of growth can be made sufficiently slow that a high level of control of diameter can be achieved simply by comparing a measured current flow with calibration data relating current to aperture size. Arrangements can be made for example for the applied voltage to be shut off when the calibration data indicates that the aperture has reached a desired size. As an illustrative example, for the 30 nm thick recesses mentioned above, it was found that slow expansion over of period of about 8 minutes is effective for growing an aperture 20 from a starting diameter of about 12 nm immediately after aperture formation (using a voltage of about 23V) to a final diameter of 43 nm. An image of the final aperture 20 is shown in FIG. 13. As can be seen, the aperture 20 is accurately circular with a smooth edge.

In an embodiment, the current limiting resistor 46 is an external resistor (e.g. a solid state resistor) positioned outside of the baths 38,40. In other embodiments, the current limiting resistor 46 may comprise a fluidic resistor or a fluidic resistor and an external resistor.

Where a current limiting resistor is provided which provides a significant reduction in voltage across the membrane 2 when the aperture is formed, only a single aperture can normally be formed per current limiting resistor. Thus, arrangements of the type shown in FIG. 12 would normally be used to form a single aperture 20. However, where fluidic resistors are used as current limiting resistors, more than one such current limiting resistor can be provided within a given bath comprising ionic solution. This makes it possible to form multiple apertures in parallel while also using current limiting resistors to enhance control of the process.

For example, a plurality of the fluidic passages 24 may be configured to operate as current limiting resistors. In this case, each of one or more of the fluidic passages 24 is configured such that when an aperture 20 is formed in the fluidic passage 24 the fluidic electrical resistance of the aperture 20 is less than 10 times the fluidic electrical resistance of the fluidic passage, optionally approximately equal to the fluidic electrical resistance of the fluidic passage 24. The fluidic passages 24 may for example be made relatively elongate. The degree of elongation of the fluidic passages may be parameterized by reference to the aspect ratio. The aspect ratio may be defined as the ratio of a length of the fluidic passage 24 to an average width of the fluidic passage 24. In the case of a cylindrical fluidic passage, the aspect ratio would simply be the ratio of the axial length of the cylinder to the diameter of the cylinder. Where the fluidic passage 24 has a more complex form, e.g. with a non-circular cross-section and/or a cross-section which varies along the length of the fluidic passage 24, an average value for width can be used. In order to provide a sufficiently high fluidic electrical resistance, the aspect ratio of the fluidic passages 24 may be greater than 1, optionally significantly higher.

An appropriate fluidic resistance of a fluidic resistor (e.g. fluidic passage 24) acting as a current limiting resistor can be achieved by appropriate design of the geometry of the fluidic resistor and selection of the resistivity of the ionic solution that will be present within the fluidic resistor. Taking for example a simple cylindrical fluidic resistor geometry, the fluidic resistance R can be expressed by the following expression:

$$R = 4\,\rho L/\pi D^2$$

Here $\rho$ is the resistivity of the solution, L is the length of the fluidic passage defining the fluidic resistor (e.g. the depth of a recess) and D is the diameter of the cylinder (e.g. the width of the recess).

Taking the example above, we can estimate the requirement for an aperture 20 formed in a 30 nm thick membrane 2 of silicon nitride and ~2MΩ limiting resistor completely defined by a cylindrical fluidic passage through a 2 μm thick dielectric coating (silicon oxide) on top of the membrane 2. If it is a similar ·9.1 Ωcm resistivity solution on both sides, the required diameter of the fluidic resistor is approximately 340 nm. This diameter and aspect ratio can be achieved by conventional lithography easily.

In some cases, when the required aperture 20 is very small and the diameter of the fluidic resistor is limited by lithography, the required aspect ratio of the fluidic resistor can be very large. For example, a ~2 nm diameter aperture 20 in a 10 nm thick membrane 2 will require 20-30 μm long fluidic channel if the diameter is limited to 100 nm. Increasing the resistivity of solution in the fluidic resistor (such as by diluting the solution or filling it with a gel or porous materials) can help reduce the aspect ratio requirement. Since there is no diffusion across the membrane 2 before dielectric breakdown, diluting the solution to increase the resistivity can proportionally reduce the required aspect ratio of the fluidic resistor if application of the voltage is stopped quickly after breakdown, before diffusion reaches the steady state. For example, 100 times increased resistivity of the solution in the fluidic resistor can lead to a lithography-friendly 200 nm diameter and 1 μm long fluidic resistor. Even in a case where the voltage is not stopped quickly enough that the diffusion does not reach the steady states, the fluidic resistance follows the following equation roughly as long as the fluidic resistor has a much larger aspect ratio than the aspect ratio of nanopore:

$$R = 4\sqrt{\rho_{cis}\rho_{trans}}L/\pi D^2$$

Here $\rho_{cis}$ and $\rho_{trans}$ are the bulk resistivity of solution in the cis and trans chamber respectively. According to this equation, a same 2 nm diameter and 10 nm thick pore only requires ~115 nm diameter and 1 μm long fluidic resistor if we fill the fluidic resistor with a solution that is 1000 times more resistive.

In the embodiments discussed above only a single current limiting resistor is provided or a plurality of identical current limiting resistors are provided (e.g. such as in FIG. 6). This is not essential. In other embodiments, a plurality of fluidic passages 24 are provided which have different fluidic electrical resistances. Where the fluidic resistances are sufficiently large to have a significant impact on the growth rates of the apertures 20 formed in the respective fluidic passages 24, this approach allows differently sized apertures 20 to be grown in parallel via the voltage applied via the first and second electrodes (i.e. simultaneously across all of the target regions 5). Apertures 20 in fluidic passages 24 having a relatively high fluidic electrical resistance will tend to grow more slowly than apertures 20 in fluidic passages 24 having a lower fluidic electrical resistance. Thus, controlled, simultaneous formation of apertures 20 having different sizes to each other is made possible.

In an embodiment, the rate of growth of an aperture 20 is controlled by controlling the ionic strength of the ionic solution in the first or second bath 38, 40, which determines the fluidic resistance in a fluidic passage 24 associated with the aperture 20. For example, by changing the ionic solution so that the fluidic resistance increases, it is possible to slow the rate of aperture growth and vice versa.

Figure 14:
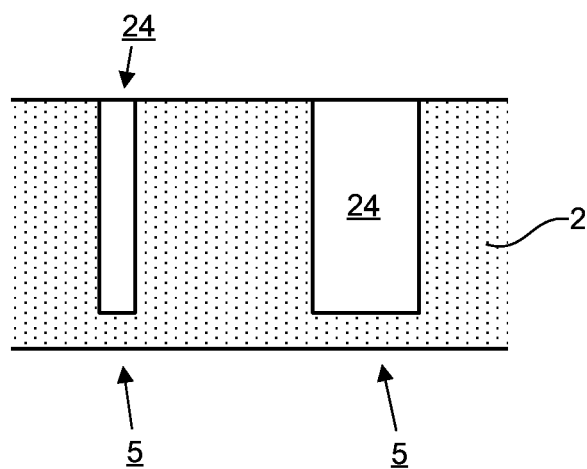
FIG. 14 shows a membrane comprising fluidic passages having different fluidic resistances.
Figure 15:
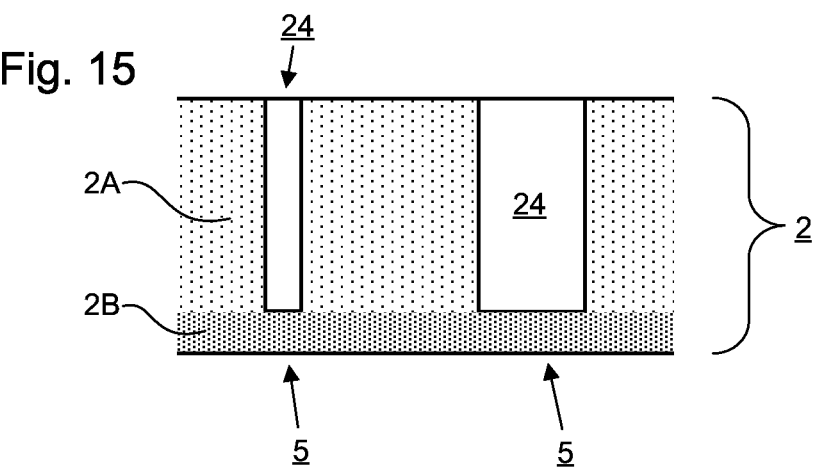
FIG. 15 shows a membrane having a layered structure to facilitate accurate formation of fluidic passages.

FIGS. 14 and 15 show schematically a portion of a membrane 2 in which fluidic passages 24 having different aspect ratios have been formed, each of these fluidic passages 24 thereby having different fluidic resistances relative to each other. The left fluidic passage 24 in this particular example had a diameter of 50 nm and the right a diameter of 100 nm. The fluidic passages 24 were formed in a 300 nm thick SiNx membrane 2. The thickness of the membrane 2 at the end of the fluidic passages 24 was 10 nm. It was found that applying 10V across the membrane 2 caused a single aperture 20 to be formed in each of the two fluidic passages 24. The current limiting effect of the narrower fluidic passage 24 meant that when the aperture 20 in the wider fluidic passage 24 reached a diameter equal to 10 nm (the thickness of the membrane material at the end of the fluidic passage 24), the aperture 20 in the narrower fluidic passage 24 only had a diameter of 5 nm.

Figure 4:
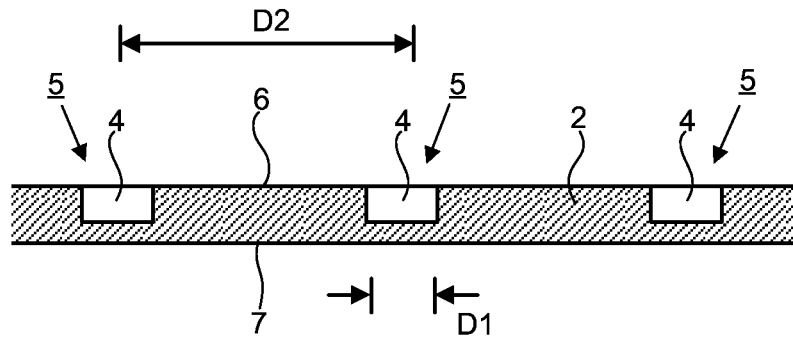
FIG. 4 is a magnified side sectional view of an embodiment in which the membrane comprises a plurality of recesses having rectangular depth profiles.
Figure 5:
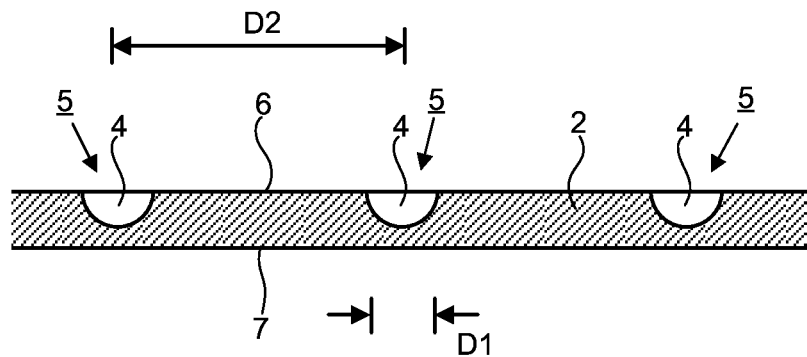
FIG. 5 is a magnified side sectional view of an embodiment in which the membrane comprises a plurality of recesses having curved depth profiles.
Figure 6:
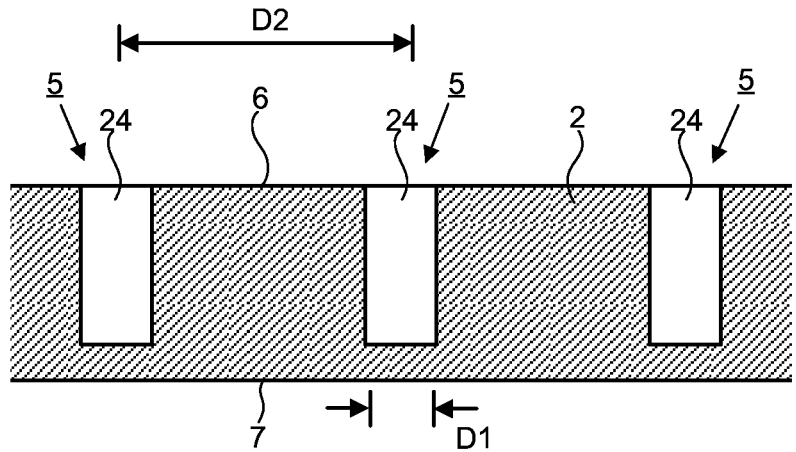
FIG. 6 is a magnified side sectional view of an embodiment in which the membrane comprises a plurality of fluidic passages having an aspect ratio greater than 1.

Providing a fluidic passage 24 having a large enough aspect ratio to provide a functionally significant fluidic electrical resistance may require a thicker membrane 2 than is required in embodiments with shallower recesses 4 (e.g. as in FIGS. 4 and 5). In the example of FIGS. 14 and 15 a 300 nm membrane 2 formed from SiNx was used, with fluidic passages 24 formed lithographically. The etch process needs to be stopped at the appropriate point to ensure the thickness of the membrane 2 at the end of the fluidic passages 24 is as required. For small thicknesses (e.g. 10 nm), it can be challenging to stop the etching process sufficiently precisely, for example where the fabrication facility has stability issues. Fabrication can be facilitated by forming the membrane 2 from a plurality of layers having different compositions which, using a suitable etchant, yield different individual etch rates. An example of such an arrangement is shown in FIG. 15. Here the membrane 2 is formed from two layers 2A and 2B of different composition. The lower layer 2B is arranged to have a thickness equal to the desired thickness of the membrane 2 at the end of the fluidic passages 24. Using an etching process in which the lower layer 2B does not etch or the etch rate is lower than for the upper layer 2A facilitates stopping of the etch process at the appropriate point. In an embodiment, by carefully choosing the material and process of making target region 5 in multilayer membrane 2 shown in FIG. 15, molecular sized apertures can be formed. In an example arrangement, membrane 2A is 300 nm thick SiNx and 2B is 2 nm thick ALD $HfO_2$. At least one fluidic passage 24 with 50 nm diameter is formed in membrane 2A by lithography and reactive ion etching. Due to the inert nature of $HfO_2$ film, fluidic passage 24 can be etched through the whole SiNx 2A layer and stop naturally at $HfO_2$ forming uniform 2 nm $HfO_2$ only target region 5. By choosing the appropriate fluidic conductivity and breakdown voltage, 1 nm diameter and 2 nm long $HfO_2$ apertures can be formed in the target regions in parallel.

Although discussed here in the context of forming elongate fluidic passages 24, the use of a membrane 2 formed from multiple layers of different compositions can be used more generally to achieve accurate thicknesses of target regions 5, recesses 4 and/or fluidic passages 24 of any form, due to different etching rates of the individual layers. Interfaces between layers of different compositions, which correspond to sudden changes or stopping of an etching process when the interfaces are reached, can be used to define any boundaries of structures formed in the membrane 2 (e.g. bottoms of recesses 4 or ends of fluidic passages 24). In an embodiment, the membrane 2 comprises a first layer (e.g. the upper layer 2A in FIG. 15) and a second layer (e.g. the lower layer 2B in FIG. 15), each of one or more recesses 4 or fluidic passages 24 is formed by removing a portion of the first layer down to the interface (at least) between the first layer and the second layer (e.g. to a depth that is level with or slightly beyond the interface between the upper layer 2A and the lower layer 2B in FIG. 15), such that the boundary is formed by a surface of the second layer (e.g. an upper surface of the exposed portion of the lower layer 2B in FIG. 15), and the second layer (e.g. the lower layer 2B in FIG. 15) is formed by atomic layer deposition. In embodiments, an aperture is formed by dielectric breakdown through at least a portion of the second layer (e.g. the lower layer 2B in FIG. 15). As explained in the introductory part of the description, atomic layer deposition allows very uniform and precise thickness control at resolutions of the order of ~1 Å. Materials which are inert to many reactive ion etch (RIE) processes can be applied using atomic layer deposition. The level of control provided by atomic layer deposition is higher than can be achieved typically using alternative film growth techniques. The length of the aperture, which is dictated by the thickness of the layer or layers in which the aperture is formed (e.g. the lower layer 2B in FIG. 15), can be controlled with high accuracy. More details about example configurations for the second layer (e.g. materials and sub-layers) are given below.

Various methods can be used to form the recesses 4 or fluidic passages 24 in the membrane 2. These may include lithography (e.g. using a mask-based or maskless system) and etching as described above. E-beam lithography may be used. Reactive ion etching may be used. Ion beam sculpting may be used.

In an embodiment, fluidic passages 24 are provided using a porous layer which comprises pores that allow the ionic solution to pass from one side of the porous layer to the other side of the porous layer. The pores in this case are fluidic passages. This approach is a convenient way of providing fluidic passages 24 of high aspect ratio, due to the naturally narrow form adopted by pores in many porous materials. If the porous layer provides the only fluidic passages 24, apertures 20 may be formed at the end of every pore of the porous layer that is traversed by the ionic solution. This may be desirable where the spatial distribution of the pores is suitable. However, in many cases it may be desired to form apertures 20 that are spaced apart differently (e.g. further apart), and/or are provided in different numbers (e.g. fewer), than the pores of the porous layer. In this case, the porous layer may be provided in combination with a layer which comprises other fluidic passages 24 which define where the apertures 20 will be formed. In this case, the porous layer may provide a plurality of fluidic passages 24 which are fluidically in parallel with each other but in series with a further fluidic passage 24 provided in a separate layer which defines where the aperture 20 will be formed. The fluidic passage 24 in the separate layer will therefore have an opening which provides access to a plurality of the fluidic passages 24 provided by the porous layer. In an embodiment, the porous layer may comprise a layer of anodized aluminium oxide (AAO). AAO can be formed with very high aspect ratio pores (e.g. greater than 1000:1), spaced apart in a lattice with a lattice constant of several hundred nanometres. The pore diameter and lattice constant can be tuned by forming the AAO on a suitably pre-patterned surface.

In another embodiment, fluidic passages 24 acting as current limiting resistors may be formed as channels within a layer of PDMS, oxide, and/or nitride.

Embodiments have been described which allow membranes 2 to be formed which comprise a plurality of target regions 5 in each of which an aperture 20 is formed. Each target region 5 comprises a recess 4 or a fluidic passage 24 defining where the aperture 20 will be formed. Each aperture 20 is located within a different one of the target regions 5 and has a diameter determined by the resistance of any limiting resistor, the voltage regime applied and/or the thickness of the target region 5. The diameter may be equal to or greater than a minimum thickness of the membrane material separating the first and second baths where thickness is used as a primary means to control the diameter. Alternatively, the diameter can be made smaller than the thickness of the membrane material.

Figure 16:
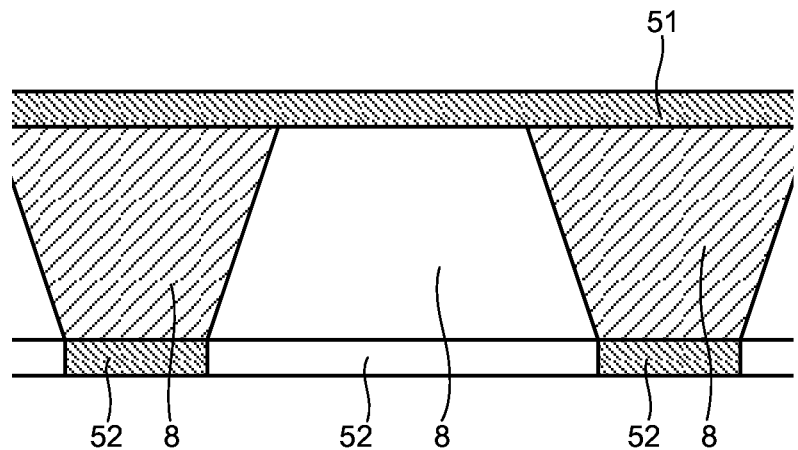
FIGS. 16-19 are schematic side sectional views depicting stages in a method of manufacturing two example membrane assemblies, depicted respectively in FIGS. 18 and 19.

FIGS. 16-19 depict steps in an example method of manufacturing a membrane assembly 36 in which atomic layer deposition is used to form a membrane 2. The membrane 2 is suitable for allowing formation of one or more apertures using dielectric breakdown according to any of the embodiments described herein. FIG. 16 shows an arrangement which may be formed in the same way as the membrane assembly 36 described above with reference to FIG. 1, except that the arrangement of FIG. 16 does not yet have any recesses 4 formed in a membrane. The upper covering layer 51 in FIG. 16 may be formed in the same way as the membrane 2 of FIG. 1 (e.g. from SiNx). The lower covering layer 52 of FIG. 16 may be formed in the same way as layer 10 in FIG. 1 (e.g. from SiNx).

Figure 17:
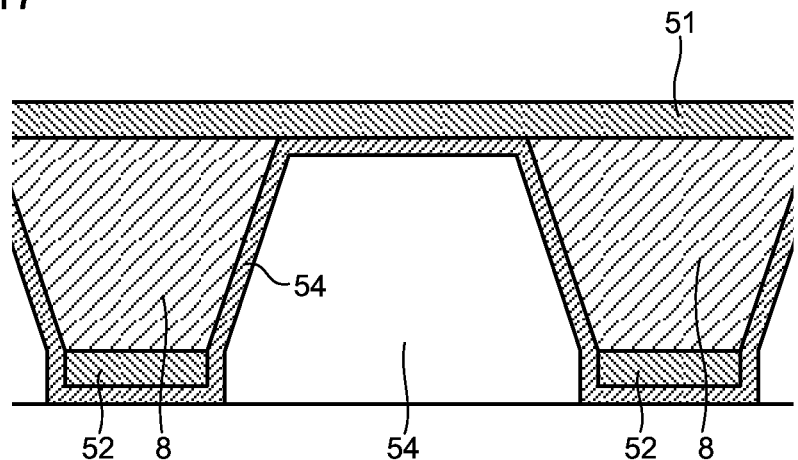

In a subsequent processing step, atomic layer deposition is used to deposit an ALD layer 54 to provide the arrangement shown in FIG. 17. Atomic layer deposition, which may be referred to as ALD, is a known technique for depositing thin films of material. The following is one example of a review paper on this topic: Steven M. George, "Atomic Layer Deposition: An Overview", Chem. Rev. 2010, 110, 111-131.

In a subsequent processing step, a fluidic passage 24 is formed in the upper covering layer 51, for example by lithography followed by a reactive ion etch. The fluidic passage 24 may be formed, for example, by etching through the upper covering layer 51 to the interface between the upper covering layer 51 and the ALD layer 54. The membrane assembly 36 shown in FIG. 18 is thereby provided.

In an alternative subsequent processing step, starting from the arrangement of FIG. 17, a recess 4 is formed in the upper covering layer 51, for example by lithography followed by a reactive ion etch. The recess 4 may be formed, for example, by etching through the upper covering layer 51 to the interface between the upper covering layer 51 and the ALD layer 54. The membrane assembly 36 shown in FIG. 19 is thereby provided.

Variations on the above processing are possible. For example, the ALD layer 54 could be deposited at an earlier stage, for example prior to processing of a wafer to form the layer 8 (e.g. by KOH etching to selectively remove portions of the wafer to form the layer 8, which make the structure more fragile) and/or prior to growth of the upper covering layer 51 (e.g. SiNx). The ALD layer 54 may even be sandwiched between two layers forming all or part of the upper covering layer 51 (e.g. between two SiNx layers). Forming the ALD layer 54 earlier may desirably reduce the number of processing steps that need to be carried out while the membrane assembly is in a relatively fragile state (e.g. while thin membranes are present and/or after a wafer has been processed to form the layer 8).

Figure 18:
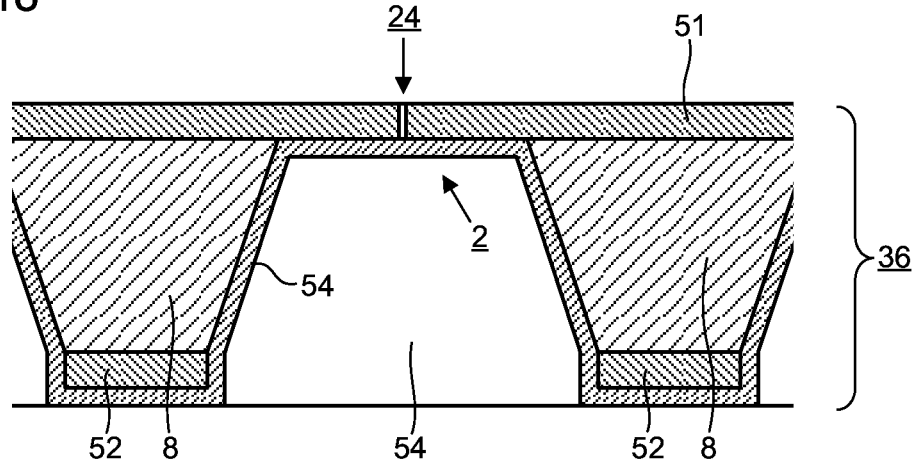
Figure 19:
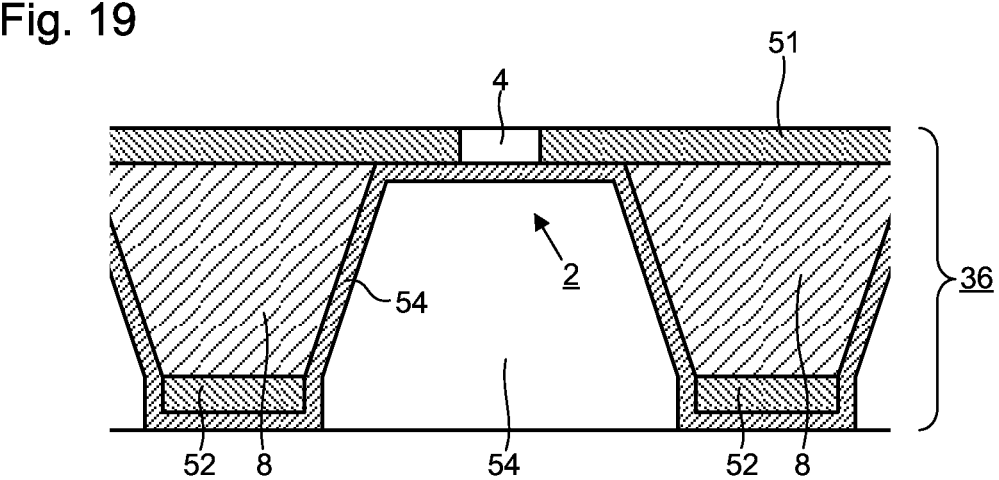

The membrane assemblies 36 shown in FIGS. 18 and 19 are examples in which a membrane 2 comprises a first layer (the upper covering layer 51 in FIGS. 18 and 19) and a second layer (the ALD layer 54 in FIGS. 18 and 19), and the second layer is formed by atomic layer deposition.

Figure 20:
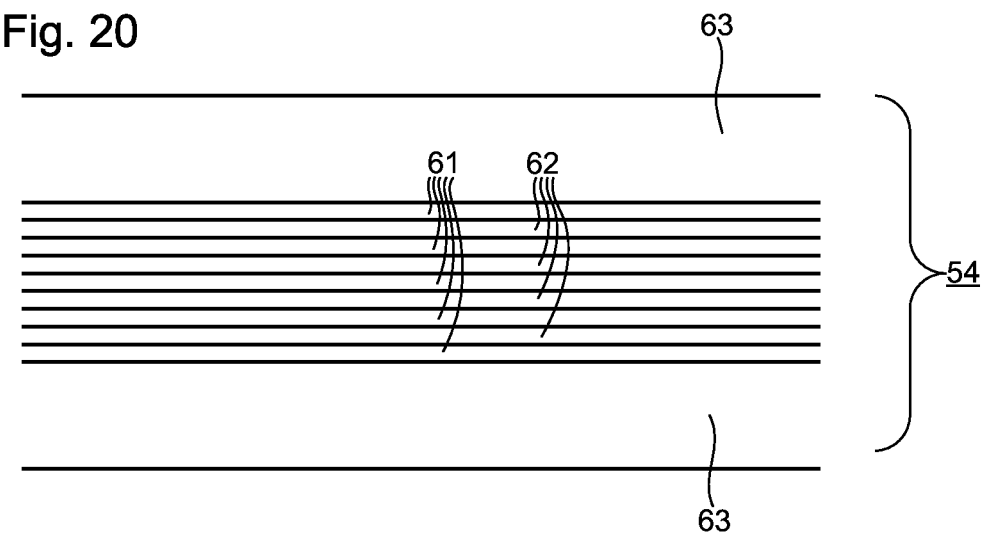
FIG. 20 is a schematic side sectional view of a portion of a membrane comprising a repeating sequence of sub-layers, and protective layers.
Figure 21:
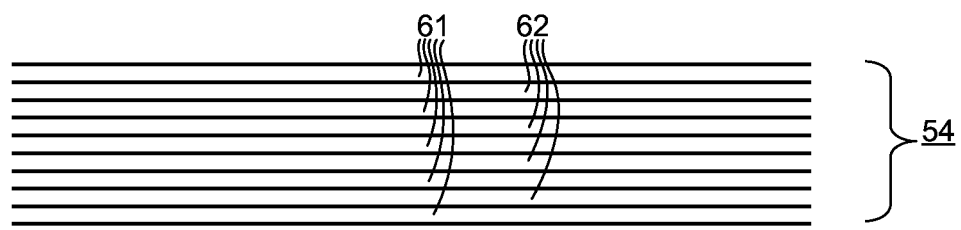
FIG. 21 is a schematic side sectional view of a portion of a membrane comprising a repeating sequence of sub-layers.

In an embodiment, examples of which are depicted in FIGS. 20 and 21, the second layer (ALD layer 54) comprises a plurality of sub-layers 61,62. Each of the sub-layers 61,62 is formed by atomic layer deposition. In an embodiment, at least two of the sub-layers 61,62 have a different composition relative to each other. Arranging for at least two of the sub-layers 61,62 to have a different composition relative to each other has been found to improve the stability of the sub-layers 61,62 during use.

In an embodiment, the plurality of sub-layers 61,62 comprises a sequence of sub-layers 61,62 that repeats a plurality of times, each repeating sequence comprising at least a first sub-layer 61 and a second sub-layer 62 directly adjacent to the first sub-layer 61. The first sub-layers 61 have a different composition to the second sub-layers 62. In the embodiment shown, each unit of the repeating sequence consists of a single first sub-layer 61 and a single second sub-layer 62 but this is not essential. In other embodiments, each repeating unit may comprise more than two sub-layers (e.g. three sub-layers, four sub-layers, or more). In an embodiment, all of the first sub-layers 61 have the same composition as each other and all of the second sub-layers 62 have the same composition as each other. In FIGS. 20 and 21, a repeating sequence comprising four units, each consisting of a first sub-layer 61 and a second sub-layer 62 is shown for ease of depiction (with an additional first sub-layer 61 being provided so that the two outermost surfaces of the plurality of sub-layers have the same composition). In practice a larger number of sub-layers will normally be provided. In an embodiment, each of the first and second sub-layers 61,62 is formed using four or fewer cycles of atomic layer deposition, for example one cycle, two cycles, three cycles, or four cycles. It is also possible for each of one or both of the first and second sub-layers 61,62 to be formed using more than four cycles of atomic layer deposition. Each of the first and second sub-layers 61,62 will typically have a thickness of the order of ~1 Å per cycle of atomic layer deposition used to create them. The number of first and second sub-layers 61,62 (and any other sub-layers that are provided) is chosen to provide a desired overall thickness for the plurality of sub-layers. The thickness of the plurality of sub-layers 61,62 defines the length of any aperture formed through the plurality of sub-layers 61,62. In an embodiment, the thickness of the plurality of sub-layers 61,62 is in the range of 2-6 nm, optionally 2-4 nm, optionally 2-3 nm. In an embodiment, about 20-60 cycles of atomic layer deposition are used to form the plurality of sub-layers 61,62.

In an embodiment, the first sub-layers 61 are non-epitaxial with respect to the second sub-layers 62. Arranging for the first sub-layers 61 to be non-epitaxial with respect to the second sub-layers 62 reduces the formation of defects due to crystal growth within the sub-layers 61,62, preserving an amorphous film. Where the plurality of sub-layers comprises other sub-layers, it is preferably arranged that all sub-layers are non-epitaxial with respect to any directly adjacent sub-layers.

The first sub-layers 61 and the second sub-layers 62 can be formed from a wide range of different materials. In an embodiment, the first sub-layers 61 comprise $HfO_2$ and the second sub-layers 62 comprise $Al_2O_3$. $HfO_2$ has good dielectric properties. These two materials are compatible with atomic layer deposition and are non-epitaxial with respect to each other.

In an embodiment, as shown for example in FIG. 20, the second layer (ALD layer 54) is formed with a protective layer 63 on one or both sides of the repeating sequence of sub-layers 61,62. The protective layer 63 protects the repeating sequence of sub-layers 61,62 from processing steps (e.g. reactive ion etching steps) used to form other features of the membrane assembly 36, for example removal of a portion of the first layer (upper covering layer 51 in FIGS. 18 and 19), such as processing steps (e.g. reactive ion etching steps) to form a fluidic passage (as in FIG. 18) or processing steps (e.g. reactive ion etching steps) to form a recess 4 (as in FIG. 19). In an embodiment, the protective layer 63 comprises $Al_2O_3$. $Al_2O_3$ is resistant to reactive ion etching but is easy to remove by wet etching. In an embodiment, the protective layer 63 has a thickness of about 5-10 nm. In an embodiment, the protective layer 63 is formed using about 50-100 cycles of atomic layer deposition. In an embodiment, the protective layer 63 is removed prior to the formation of the aperture to form a freestanding membrane comprising the repeating sequence of sub-layers 61,62. In the case where the first sub-layers 61 comprise $HfO_2$ and the second sub-layers 62 comprise $Al_2O_3$, the removal of the protective layer 63 will result in a repeating sequence of sub-layers 61,62 and an additional layer, such that the two outermost sub-layers are both first sub-layers 61 (as shown in FIGS. 20 and 21). An aperture is subsequently formed by dielectric breakdown through the freestanding membrane.

In an embodiment, the second layer (ALD layer 54) is annealed prior to forming an aperture by dielectric breakdown. The annealing is configured to remove any water trapped in the second layer after the atomic layer deposition process. The annealing thereby improves the quality of the second layer (e.g. by increasing uniformity or reducing defect concentration). The anneal may be performed below a temperature at which significant crystallization in the sub-layers might occur. Alternatively, the anneal may be performed at higher temperatures.

In an embodiment, one or more of the apertures 20 formed using the methods and apparatus discussed above, or according to other embodiments, are used to sense a molecular entity by performing a measurement (e.g. an electrical measurement or an optical measurement) that is dependent on an interaction between the molecular entity and the aperture. In an embodiment a sensing apparatus is provided having a plurality of the apertures 20 thus formed and a measurement system configured to sense a molecular entity in each of the apertures 20 by performing a measurement that is dependent on an interaction between the molecular entity and the aperture 20. Sensing of molecular entities can provide the basis for identifying single molecules and molecular entities. There are a wide range of possible applications, such as sequencing of DNA or other nucleic acids; sensing of chemical or biological molecules for security and defence; detection of biological markers for diagnostics; ion channel screening for drug development; and label free analysis of interactions between biological molecules.

The molecular entity may be polymeric such as an amino acid, peptide, polypeptide, a protein or a polynucleotide. The polynucleotide may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. The polynucleotide can be a nucleic acid, such as deoxyribonucleic acid (DNA) or ribonucleic acid (RNA). The polynucleotide can comprise one strand of RNA hybridised to one strand of DNA. The molecular entity may comprise a single stranded or double stranded polynucleotide. The polynucleotide may be partially double stranded. The polynucleotide may be labelled with one of more of a fluorescent label, an optical label, a magnetic species or a chemical species, wherein detection of the species or label is indicative of the polynucleotide. Nucleic acid probes may be hybridised to the polynucleotide and resultant structure detected by translocation through an aperture of the array, such as disclosed in published application WO2007/041621. The polynucleotide may be labelled with one or more acceptor labels, which interact with one or more donor labels attached to an aperture of the array, such as disclosed by published application WO2011/040996. The polynucleotide may be any synthetic nucleic acid known in the art. The molecular entity may be an aptamer. The molecular entity is caused to translocate the aperture and the interactions between the molecular entity and the aperture measured.

Translocation of the molecular entity through the aperture may be assisted by a motor protein such as a polynucleotide handling enzyme, or a polypeptide handing enzyme such as disclosed in published application WO2013/123379 Preferred enzymes are polymerases, exonucleases, helicases and topoisomerases, such as gyrases. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561). Alternatively translocation of the molecular entity through the pore may also be assisted by voltage control, such as disclosed by International Patent Application PCT/US2008/004467.

The characteristic to be determined may be a sequence characteristic of the polymer.

The solid state membrane may comprise either or both of organic and inorganic materials, including, but not limited to, microelectronic materials, whether electrically conducting, electrically semiconducting, or electrically insulating, including materials such as II-IV and III-V materials, oxides and nitrides, such as silicon nitride, $Al_2O_3$, and $SiO_2$, Si, $MoS_2$, solid state organic and inorganic polymers such as polyamide, plastics such as Teflon®, or elastomers such as two-component addition-cure silicone rubber, and glasses. A membrane may be formed from monatomic layers, such as graphene, or layers that are only a few atoms thick such as those disclosed in U.S. Pat. No. 8,698,481, and U.S. Patent Application Publication 2014/174927, both hereby incorporated by reference. More than one layer of material can be included, such as more than one graphene layer, as disclosed in U.S. Patent Application Publication 2013/309776, incorporated herein by reference. Suitable silicon nitride membranes are disclosed in U.S. Pat. No. 6,627,067, and the membrane may be chemically functionalized, such as disclosed in U.S. Patent Application Publication 2011/053284, both hereby incorporated by reference. The internal walls of the apertures may be coated with a functionalised coating, such as disclosed in published application WO2009/020682.

In a further embodiment, a biological nanopore may be provided within a solid state aperture. Such a structure is disclosed for example in U.S. Pat. No. 8,828,211, hereby incorporated by reference.

The biological pore may be a transmembrane protein pore. Transmembrane protein pores for use in accordance with the invention can be derived from beta-barrel pores or alpha-helix bundle pores. beta-barrel pores comprise a barrel or channel that is formed from beta-strands. Suitable beta-barrel pores include, but are not limited to, alpha-toxins, such as alpha-hemolysin, anthrax toxin and leukocidins, and outer membrane proteins/porins of bacteria, such as *Mycobacterium smegmatis* porin (Msp), for example MspA, MspB, MspC or MspD, lysenin, outer membrane porin F (OmpF), outer membrane porin G (OmpG), outer membrane phospholipase A and *Neisseria* autotransporter lipoprotein (NalP). alpha-helix bundle pores comprise a barrel or channel that is formed from alpha-helices. Suitable alpha-helix bundle pores include, but are not limited to, inner membrane proteins and outer membrane proteins, such as WZA and ClyA toxin. The transmembrane pore may be derived from Msp or from α-hemolysin (α-HL). The transmembrane pore may be derived from lysenin. Suitable pores derived from lysenin are disclosed in WO 2013/153359. The nanopore may be CsgG such as disclosed in WO 2016/034591.

The measurement may for example be electrical, optical or both. The electrical measurement may comprise measurement of ion flow through the apertures under a potential difference or concentration gradient. Electrical measurements may be made using standard single channel recording equipment as described in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559. Optical measurements may be combined with electrical measurements (Soni G V et al., Rev Sci Instrum. 2010 January; 81(1):014301).

The sensing apparatus may comprise a measurement system arranged as disclosed in any of WO-2008/102210, WO-2009/07734, WO-2010/122293, WO-2011/067559 or WO2014/04443. The sensing apparatus may comprise electrodes arranged on each side of the membrane in order to measure an ion current through an aperture under a potential difference. The electrodes may be connected to an electrical circuit which includes a control circuit arranged to supply a voltage to the electrodes and a measurement circuit arranged to measure the ion flow. A common electrode may be provided to measure ion flow through the apertures between the common electrode and electrodes provided on the opposite side of the membrane.

Fluid chambers provided on either side of the nanopore array may be referred to as the cis and trans chambers. The molecular entity to be determined by the array of nanopores is typically added to the cis chamber comprising the common electrode. Separate trans chambers may be provided on the opposite side of the array, each trans chamber comprising an electrode wherein ion flow through each aperture is measured between an electrode of the trans chamber and the common electrode.

Depending upon the aperture length (the distance between the two sides of the membrane), one or more polymer units may be present in the pore at any particular time and the measurement carried out may be dependent on a group of k polymer units, where k is an integer. A group of k polymer units where k is greater than one may be referred to as a k-mer. Conceptually, this might be thought of as the measurement system having a "blunt reader head" that is bigger than the polymer unit being measured. Determination of a sequence characteristic of k polymer units involving the measurement of k-mers may be carried out by methods disclosed by International Patent Applications PCT/GB2012/052343 and PCT/GB2013/050381. Alternatively, determination of sequence information or molecular sequence classification may be carried out using an artificial neural network (ANN).

Any measurement system used may be linked to or comprise a processor such as an ASIC, FPGA, or computer. Analysis of the measurements may be carried out in the sensing apparatus, alternatively it may be done remotely, such as by a cloud based system.

Suitable conditions for measuring ionic currents through aperture pores are known in the art. The method is typically carried out with a voltage applied across the membrane and aperture. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 2V. It is possible to increase discrimination between different nucleotides by an aperture by using an increased applied potential. As an alternative to measurement of an ionic current, measurement of a conductance or resistance may be carried out.

Alternative or additional measurements associated with movement of the molecular entity with respect to the aperture may be carried out, such as measurement of a tunnelling current across the aperture (Ivanov A P et al., Nano Lett. 2011 Jan. 12; 11(1):279-85), or a field effect transistor (FET) device, such as disclosed by WO 2005/124888, U.S. Pat. No. 8,828,138, WO 2009/035647, or Xie et al, Nat Nanotechnol. 2011 Dec. 11; 7(2): 119-125. The measurement device may be an FET nanopore device comprising source and drain electrodes to determine the presence or passage of a molecular entity in the apertures. An advantage of employing an FET nanopore device, namely one employing FET measurements across the apertures, or one employing measurement of a tunnelling current across the aperture, is that the measurement signal is very local to a particular aperture and therefore a device comprising a shared trans chamber may be employed. This greatly simplifies the construction of the device without the need to provide separate trans chambers for each aperture, such as one for the measurement of ion flow through the apertures, as described above. As a result, very high densities of apertures in the array may be conveniently provided, for example an array comprising apertures having a pitch of less than 10 ∥m and a density of $10^6$ apertures /$cm^2$.

Sensing methods, particularly those involving measurement of an ionic current, may be performed in a sensing solution comprising various different charge carriers, including for example metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M. High salt concentrations provide a high signal to noise ratio and allow for currents indicative of the presence of a nucleotide to be identified against the background of normal current fluctuations.

The sensing solution may comprise a buffer. Any buffer may be used. Typically, the buffer is phosphate buffer. The sensing solution may comprise a buffer to regulate the pH. Any buffer suitable for the desired pH may be used. Maintaining a particular pH may be desirable for a variety of reasons, including maintaining consistent motor protein and biological nanopore performance, maintaining a consistent surface charge on solid-state membranes, and maintaining a consistent charge (and thus a consistent driving force and capture rate) on target analytes such as DNA.

Either or both of the first and second ionic solutions used for forming the apertures may also be used as the sensing solution. Either or both of the first and second ionic solutions may comprise a biological fluid containing ions (e.g. from salt), such as blood or plasma.

The ability to be able to form porous structures comprising arrays of apertures enables a large range of potential applications, such as for example the provision of structures that are initially present in a non-porous state but which may be activated in situ by dielectric breakdown to make them porous. As nanopores may be fragile and/or have a limited lifetime, generating pores in situ by dielectric breakdown enables a much longer shelf life when the structures are stored and distributed in the non-porous state. The non-porous structures may be used for example to initially contain a species which is subsequently released through the porous structure created by dielectric breakdown. Example uses are filter membranes, drug delivery and printing applications. The species to be delivered may comprise an ion or molecule. The molecule may be any such as a drug. The porous membrane may act an electrochemical frit, wherein formation of the apertures provides an ionic connection between the baths. The ability to form a porous membrane in situ enables a species to be contained within either the first or second bath until required or is able to limit the ability of a species provided in one bath to interfere with a species present in the second bath. For example, the first bath may contain a reference electrode such as Ag/AgCl, wherein it is desirable to limit the interaction of silver ions with a biochemical reagent present in the second bath.

For example, in an embodiment methods and apparatus are provided in which a substance is delivered from a first bath 38 to a second bath 40 and/or vice-versa. The first and second baths 38,40 may for example be configured as described above with reference to FIG. 11 or 12 or in other ways. The first and second baths 38,40 are separated from each other by a solid state membrane 2. The delivery is initiated in a highly controllable manner by forming of one or a plurality of apertures in the solid state membrane 2 using methods or apparatus according to any of the embodiments discussed above, or other embodiments.

For example, in an embodiment methods and apparatus are provided in which a filtering property of a filter comprising a solid state membrane 2 is modified. The filtering property is modified in a highly controllable manner by forming of one or a plurality of apertures in the solid state membrane 2 using methods or apparatus according to any of the embodiments discussed above, or other embodiments.

For example, in an embodiment methods and apparatus are provided in which a first reactive species is brought into contact with a second reactive species. The bringing together of these species may cause a desired reaction to occur between the species. The first reactive species is provided in a first bath 38. The second reactive species is provided in a second bath 40. The first and second baths 38,40 may for example be configured as described above with reference to FIG. 11 or 12 or in other ways. The first and second baths 38,40 are separated from each other by a solid state membrane 2. The reactive species are brought together in a highly controllable manner by forming of one or a plurality of apertures in the solid state membrane 2 using methods or apparatus according to any of the embodiments discussed above, or other embodiments.

The features defined in the claims may be used together in any combination.

The invention claimed is:

1. A method of forming a plurality of apertures in a solid state membrane using dielectric breakdown, wherein the membrane comprises a first surface area portion on one side of the membrane and a second surface area portion on the other side of the membrane, and each of a plurality of target regions comprises a recess or fluidic passage in the membrane that opens out into the first or second surface area portion, the method comprising:
contacting all of the first surface area portion of the membrane with a first bath comprising ionic solution and all of the second surface area portion with a second bath comprising ionic solution; and
applying a voltage across the membrane via first and second electrodes in respective contact with the first and second baths comprising ionic solutions to form an aperture at each of a plurality of the target regions in the membrane;
wherein:
the membrane comprises a first layer and a second layer;
the formation of an aperture at each of the plurality of target regions occurs by dielectric breakdown through at least a portion of the second layer;
the second layer is formed by atomic layer deposition; and
the method further comprises annealing the second layer before forming the apertures.

2. The method of claim 1, wherein a single aperture is formed in each of the target regions.

3. The method of claim 2, wherein the aperture in each target region is grown until a diameter of the aperture is equal to or greater than a minimum thickness of membrane material separating the first bath from the second bath in the target region.

4. The method of claim 1, wherein the membrane comprises a plurality of layers and a boundary of each of one or more of the recesses or fluidic passages is located at an interface between two of the layers.

5. The method of claim 4, wherein:
each of the one or more recesses or fluidic passages is formed by removing a portion of the first layer down to the interface between the first layer and the second layer, such that said boundary is formed by a surface of the second layer.

6. The method of claim 1, wherein the second layer comprises a plurality of sub-layers, each sub-layer formed by atomic layer deposition, wherein the plurality of sub-layers comprises a sequence of sub-layers that repeats a plurality of times, each repeating sequence comprising at least a first sub-layer and a second sub-layer directly adjacent to the first sub-layer.

7. The method of claim 6, wherein the first sub-layers are non-epitaxial with respect to the second sub-layers.

8. The method of claim 7, wherein the first sub-layers comprise $HfO_2$ and the second sub-layers comprise $Al_2O_3$.

9. The method of claim 6, wherein each sub-layer in the repeating sequence is formed using four or fewer cycles of atomic layer deposition.

10. The method of claim 6, wherein:
the second layer is formed with a protective layer on one or both sides of the repeating sequence of sub-layers;
the protective layer is removed prior to the formation of the aperture in each target region in order to form a freestanding membrane comprising the repeating sequence of sub-layers in each target region; and
the aperture in each target region is formed by dielectric breakdown through the freestanding membrane.

11. The method of claim 10, wherein the protective layer is resistant to an etching process used to remove a portion of the first layer adjacent to the second layer.

12. The method of claim 10, wherein the protective layer comprises $Al_2O_3$.

13. The method of claim 1, wherein one or more of the target regions comprises a recess or fluidic passage having a depth profile in which the depth increases progressively from an edge of an opening of the recess or fluidic passage towards a central region of the recess or fluidic passage, prior to a formation of any aperture in the recess.

14. The method of claim 1, wherein one or more of the target regions comprises a fluidic passage and one or more of the fluidic passages has an aspect ratio of greater than 1, wherein the aspect ratio is defined as a ratio of a length of the fluidic passage to an average width of the fluidic passage.

15. The method of claim 1, wherein one or more of the target regions comprises a fluidic passage and in each of one or more of the fluidic passages an aperture is formed which has a fluidic electrical resistance of less than 10 times the fluidic electrical resistance of the fluidic passage.

16. The method of claim 1, wherein fluidic passages having different fluidic electrical resistances are provided in different target regions, and a corresponding plurality of differently sized apertures are grown in parallel via the voltage applied via the first and second electrodes.

17. The method of claim 1, wherein one or more of the target regions comprises a recess having an average width less than 5 times an average depth.

18. The method of claim 1, wherein the applying of the voltage comprises applying a substantially constant uninterrupted voltage for a majority of a time during which the aperture is grown by the voltage.

19. The method of claim 1, wherein the applying of the voltage comprises the following:
    applying a first voltage that initiates aperture formation; and
    growing each formed aperture using a second voltage that is lower than the first voltage.

20. The method of claim 19, wherein the second voltage is lower than would be necessary to initiate aperture formation.

21. The method of claim 19, wherein the applying of the voltage further comprises growing each formed aperture using a third voltage which is equal to or higher than the first voltage, subsequent to the step of growing each formed aperture using the second voltage.

* * * * *

UNITED STATES PATENT AND TRADEMARK OFFICE
CERTIFICATE OF CORRECTION

| | | |
|---|---|---|
| PATENT NO. | : 10,596,523 B2 | Page 1 of 1 |
| APPLICATION NO. | : 15/575798 | |
| DATED | : March 24, 2020 | |
| INVENTOR(S) | : Ping Xie et al. | |

It is certified that error appears in the above-identified patent and that said Letters Patent is hereby corrected as shown below:

On the Title Page

(73) Assignee: Oxford Nanopore Inc.
Should be:
(73) Assignee: Oxford Nanopore Inc., Cambridge, MA (US)

Signed and Sealed this
Sixth Day of April, 2021

Drew Hirshfeld
*Performing the Functions and Duties of the
Under Secretary of Commerce for Intellectual Property and
Director of the United States Patent and Trademark Office*